United States Patent
Leonhardt

(10) Patent No.: US 11,167,141 B2
(45) Date of Patent: Nov. 9, 2021

(54) BIOELECTRIC BLOOD PRESSURE MANAGEMENT

(71) Applicant: Leonhardt Ventures LLC, Corona Del Mar, CA (US)

(72) Inventor: Howard J. Leonhardt, Playa Vista, CA (US)

(73) Assignee: LEONHARDT VENTURES LLC, Corona Del Mar, CA (US)

( * ) Notice: Subject to any disclaimer, the term of this patent is extended or adjusted under 35 U.S.C. 154(b) by 247 days.

(21) Appl. No.: 16/137,440

(22) Filed: Sep. 20, 2018

(65) Prior Publication Data

US 2019/0022396 A1 Jan. 24, 2019

Related U.S. Application Data

(63) Continuation-in-part of application No. 15/812,760, filed on Nov. 14, 2017, now Pat. No. 10,960,206, and
(Continued)

(51) Int. Cl.
*A61N 1/08* (2006.01)
*A61N 1/36* (2006.01)
(Continued)

(52) U.S. Cl.
CPC ..... *A61N 1/36117* (2013.01); *A61M 39/0208* (2013.01); *A61N 1/37205* (2013.01);
(Continued)

(58) Field of Classification Search
CPC .. A61N 1/36002; A61N 1/08; A61N 1/36017; A61N 1/3629; A61N 1/375;
(Continued)

(56) References Cited

U.S. PATENT DOCUMENTS

| D273,893 S | 5/1984 | Weitzman |
|---|---|---|
| 4,622,952 A | 11/1986 | Gordon |

(Continued)

FOREIGN PATENT DOCUMENTS

| CA | 2685161 A1 | 10/2007 |
|---|---|---|
| EP | 0603451 A1 | 6/1994 |

(Continued)

OTHER PUBLICATIONS

Bang et al., "Attenuation of Hypertension by C-Fiber Stimulation of the Human Median Nerve and the Concept-Based Novel Device," Scientific Reports, vol. 8, (2018), 12 pages.

(Continued)

*Primary Examiner* — Mark W. Bockelman
(74) *Attorney, Agent, or Firm* — TraskBritt

(57) ABSTRACT

Described are a system and method that utilize bioelectric signaling to balance electrical potentials in a subject's body via neuro-hormonal circuit loops, to increase elasticity of the subject's arteries to promote protein release to dampen arterial blood pressure, and to change arterial electrical charges to reduce narrowing of the arteries. The described system is designed to localize and stimulate the fibers inside the vagus nerve without inadvertent stimulation of non-baroreceptive fibers causing side effects like bradycardia and bradypnea. The system also controls release of specific proteins known to lower blood pressures including tropoelastin (known to increase elasticity in the aorta and other peripheral blood vessels).

18 Claims, 11 Drawing Sheets

Related U.S. Application Data a continuation-in-part of application No. 15/460,129, filed on Mar. 15, 2017, now Pat. No. 10,646,644.

(60) Provisional application No. 62/308,702, filed on Mar. 15, 2016, provisional application No. 62/363,012, filed on Jul. 15, 2016, provisional application No. 62/364,472, filed on Jul. 20, 2016, provisional application No. 62/375,271, filed on Aug. 15, 2016, provisional application No. 62/385,124, filed on Sep. 8, 2016, provisional application No. 62/454,521, filed on Feb. 3, 2017, provisional application No. 62/352,930, filed on Jun. 21, 2016.

(51) Int. Cl.
| | |
|---|---|
| A61M 39/02 | (2006.01) |
| A61N 1/372 | (2006.01) |
| A61M 39/00 | (2006.01) |
| A61N 1/362 | (2006.01) |
| A61M 5/142 | (2006.01) |
| A61B 5/021 | (2006.01) |
| A61B 5/00 | (2006.01) |
| A61B 5/0537 | (2021.01) |

(52) U.S. Cl.
CPC .......... A61B 5/002 (2013.01); A61B 5/02108 (2013.01); A61B 5/0537 (2013.01); A61B 5/4836 (2013.01); A61M 5/14276 (2013.01); A61M 2039/0036 (2013.01); A61M 2202/07 (2013.01); A61M 2205/05 (2013.01); A61M 2205/50 (2013.01); A61M 2205/502 (2013.01); A61N 1/36002 (2017.08); A61N 1/3629 (2017.08)

(58) Field of Classification Search
CPC .......... A61N 1/36117; A61N 1/37205; A61M 39/0208; A61M 2202/07; A61M 2039/0036; A61M 5/14276; A61M 2205/502; A61M 2205/05; A61M 2205/50; A61B 5/02108; A61B 5/002; A61B 5/4836; A61B 5/0537
See application file for complete search history.

(56) References Cited

U.S. PATENT DOCUMENTS

| | | | |
|---|---|---|---|
| 4,976,733 A | 12/1990 | Girardot | |
| 5,211,622 A | 5/1993 | Liboff et al. | |
| 5,543,318 A | 8/1996 | Smith et al. | |
| 5,693,029 A | 12/1997 | Leonhardt | |
| 5,713,917 A | 2/1998 | Leonhardt et al. | |
| 5,725,377 A | 3/1998 | Lemler et al. | |
| 5,817,139 A | 10/1998 | Hiroyuki | |
| 5,957,949 A | 9/1999 | Leonhardt et al. | |
| 6,344,052 B1 | 2/2002 | Greenan et al. | |
| 6,618,625 B2 | 9/2003 | Silverstone | |
| 6,957,106 B2 | 10/2005 | Schuler et al. | |
| 6,988,004 B2 | 1/2006 | Kanno et al. | |
| 7,029,276 B2 | 4/2006 | Mao | |
| 7,136,699 B2 | 11/2006 | Palti | |
| 7,341,062 B2 | 3/2008 | Chachques et al. | |
| 7,483,749 B2 | 1/2009 | Leonhardt et al. | |
| 7,686,799 B2 | 3/2010 | Leonhardt et al. | |
| 7,881,784 B2 | 2/2011 | Pasricha et al. | |
| 8,041,428 B2 * | 10/2011 | Errico ............... | A61N 1/36053 607/44 |
| 8,133,267 B2 | 3/2012 | Leonhardt et al. | |
| 8,166,976 B2 | 5/2012 | Webster et al. | |
| 8,226,407 B2 | 7/2012 | Hanewinkel et al. | |
| 8,465,533 B2 | 6/2013 | Palti | |
| 8,639,361 B2 | 1/2014 | Nathanson | |
| 8,656,930 B2 | 2/2014 | Schuler et al. | |
| 8,660,669 B2 | 2/2014 | Nemeh et al. | |
| 8,738,144 B2 | 5/2014 | Schneider | |
| 8,909,346 B2 | 12/2014 | Chalmers | |
| 8,945,104 B2 | 2/2015 | Boone et al. | |
| 9,032,964 B2 | 5/2015 | Schuler et al. | |
| 9,533,170 B2 | 1/2017 | Dye et al. | |
| 9,545,331 B2 | 1/2017 | Ingemarsson-Matzen | |
| D778,449 S | 2/2017 | Ingemarsson-Matzen | |
| 9,656,096 B2 | 5/2017 | Pilla | |
| 9,662,184 B2 | 5/2017 | Lowe | |
| 9,687,383 B2 | 6/2017 | Ingemarsson-Matzen | |
| D832,447 S | 10/2018 | Wiffen | |
| D881,399 S | 4/2020 | Ingemarsson-Matzen | |
| 10,646,644 B2 | 5/2020 | Leonhardt et al. | |
| 2002/0143373 A1 | 10/2002 | Courtnage et al. | |
| 2003/0032998 A1 | 2/2003 | Altman | |
| 2003/0220556 A1 | 11/2003 | Porat et al. | |
| 2004/0010231 A1 | 1/2004 | Leonhardt et al. | |
| 2004/0115587 A1 | 6/2004 | Breining et al. | |
| 2004/0147906 A1 | 7/2004 | Voyiazis et al. | |
| 2004/0236238 A1 | 11/2004 | Schuler et al. | |
| 2005/0171578 A1 | 8/2005 | Leonhardt | |
| 2006/0030908 A1 | 2/2006 | Powell et al. | |
| 2006/0100553 A1 | 5/2006 | Lodin | |
| 2007/0167984 A1 | 7/2007 | Kieval et al. | |
| 2007/0190028 A1 | 8/2007 | Qu et al. | |
| 2007/0265680 A1 | 11/2007 | Liu et al. | |
| 2008/0227046 A1 | 9/2008 | Lowe et al. | |
| 2008/0243060 A1 | 10/2008 | Hartmann et al. | |
| 2010/0082027 A1 | 4/2010 | Chalmers | |
| 2010/0184183 A1 | 7/2010 | Schussler et al. | |
| 2012/0156648 A1 | 6/2012 | Kaufman et al. | |
| 2013/0253413 A1 | 9/2013 | Levine et al. | |
| 2014/0023983 A1 | 1/2014 | Lowe et al. | |
| 2014/0214115 A1 | 7/2014 | Greiner et al. | |
| 2014/0214116 A1 | 7/2014 | Peterson et al. | |
| 2014/0214124 A1 | 7/2014 | Greiner et al. | |
| 2014/0214144 A1 | 7/2014 | Peterson et al. | |
| 2017/0028184 A1 | 2/2017 | Godden et al. | |
| 2017/0036032 A1 | 2/2017 | Schuler et al. | |
| 2017/0112983 A1 | 4/2017 | Thorne et al. | |
| 2017/0266371 A1 | 9/2017 | Leonhardt et al. | |
| 2017/0274206 A1 | 9/2017 | Leonhardt | |
| 2018/0064935 A1 | 3/2018 | Leonhardt et al. | |
| 2018/0071135 A1 | 3/2018 | Ingemarsson-Matzen | |
| 2019/0015661 A1 | 1/2019 | Leonhardt et al. | |
| 2019/0022389 A1 | 1/2019 | Leonhardt | |
| 2019/0022396 A1 | 1/2019 | Leonhardt | |
| 2020/0030136 A1 | 1/2020 | Hernandez | |
| 2020/0289826 A1 | 9/2020 | Leonhardt | |
| 2020/0324106 A1 | 10/2020 | Leonhardt | |
| 2020/0330753 A1 | 10/2020 | Leonhardt et al. | |

FOREIGN PATENT DOCUMENTS

| | | |
|---|---|---|
| JP | 2013-034881 A | 2/2013 |
| KR | 10-2007-0010908 A | 1/2007 |
| KR | 10-0726825 B1 | 6/2007 |
| WO | 92/17118 A1 | 10/1992 |
| WO | 2006/116728 A2 | 11/2006 |
| WO | 2007/146187 A2 | 12/2007 |
| WO | 2008/145724 A1 | 12/2008 |
| WO | 2009/021535 A1 | 2/2009 |
| WO | 2011/016629 A2 | 2/2011 |

OTHER PUBLICATIONS

Chen et al., Efficacy and Safety of Acupuncture for Essential Hypertension: A Meta-Analysis, Medical Science Monitor, vol. 24, (2018), pp. 2946-2969.

Eurekalert, UCI Study Finds Acupuncture Lowers Hypertension by Activating Natural Opioids, Available Online at < https://www.eurekalert.org/pub_releases/2016-10/uoc-usf103116.php >, (2016), 2 pages.

Fan et al., "A Review on the Nonpharmacological Therapy of Traditional Chinese Medicine with Antihypertensive Effects," Evidence-

(56) References Cited

OTHER PUBLICATIONS

Based Complementary and Alternative Medicine, vol. 2019, (2019), Article ID 1317842, 7 pages.
Flachskampf et al., "Randomized Trial of Acupuncture to Lower Blood Pressure," Circulation, vol. 115, (2007), pp. 3121-3129.
Healthcmi, "Acupuncture Combats Hypertension In University of California Research," Available online at < https://www.healthcmi.com/Acupuncture-Continuing-Education-News/1688-acupuncture-c . . . >, (2016), 9 pages.
Healthcmi, "Acupuncture Controls Hypertension In Groundbreaking Trial," Available online at < https://www.healthcmi.com/Acupuncture Continuing Education News/1804 acupuncture-c . . . >, (2017), 9 pages.
Healthcmi, "UC Irvine—Acupuncture Reduces Hypertension Confirmed," Available Online at < https://www.healthcmi.com/Acupuncture-Continuing-Education-News/1792-uc-irvine-acup . . . >, (2017), 6 pages.
Li et al., "Long-Lasting Reduction of Blood Pressure by Electroacupuncture in Patients with Hypertension Randomized Controlled Trial," Medical Acupuncture, vol. 27, No. 4, (2015), pp. 253-266.
Li et al., "Repetitive Electroacupuncture Attenuates Cold-Induced Hypertension through Enkephalin in the Rostral Ventral Lateral Medulla," Scientific Reports, vol. 6, (2016), 10 pages.
Li et al., "The Mechanism of Acupuncture in Treating Essential Hypertension: A Narrative Review," International Journal of Hypertension, vol. 2019, (2019), Article ID 8676490, 10 pages.
Li, et al. "Local injection of RANKL facilitates tooth movement and alveolar bone remodelling." Oral Diseases, 25(2), 550-560. https://doi.org/10.1111/odi.13013.
Sahmeddini et al., "Electro-Acupuncture Stimulation at Acupoints Reduced the Severity of Hypotension During Anesthesia in Patients Undergoing Liver Transplantation," Journal of Acupuncture and Meridian Studies, vol. 5, Issue 1, (2012), pp. 11-14.
Tan et al., "Acupuncture Therapy for Essential Hypertension: a Network Meta-Analysis," Annals of Translational Medicine, vol. 7, (2019), pp. 1-12.
Ucirvine, "Electroacupuncture for Hypertension in Women: The Susan Samueli Center for Integrative Medicine at UC Irvine is Recruiting Patients for a Study", Principle Investigators: Dr. Stephanie Tjen-a-Looi and Dr. Shaista Malik, MOD# 20266, HS# 1999-2222, (2017), 1 page.
Vilela-Martin et al., "Effects of Transcutaneous Electrical Nerve Stimulation (TENS) on Arterial Stiffness and Blood Pressure in Resistant Hypertensive Individuals: Study Protocol for a Randomized Controlled Trial," Trials, vol. 17, (2016), pp. 1-13.
Yang et al., "Acupuncture for hypertension," Cochrane Database of Systematic Reviews, Available Online at < https://www.cochranelibrary.com/cdsr/doi/10.1002/14651858.CD008821.pub2/full >, (2018), 4 pages.
Zupan et al. "The relationship between osteoclastogenic and anti-osteoclastogenic pro-inflammatory cytokines differs in human osteoporotic and osteoarthritic bone tissues," Journal of Biomedical Science, 2012, 19:28 (DOI: 10.1186/1423-0127-19-28).
Zhang et al. "Exosomes derived from human embryonic mesenchymal stem cells promote osteochondral regeneration", Osteoarthritis and Cartilage, vol. 24, Issue 12, Dec. 2016, pp. 2135-2140.
Yamakazi et al., "Hair cycle-dependent expression of hepatocyte growth factor (HGF) activator, other proteinases, and proteinase inhibitors correlates with the expression of HGF in rat hair follicles", J Investig Dermatol Symp Proc., 4 (3):312-5 (Dec. 1999).
Yamaguchi, "RANK/RANKL/OPG during orthodontic tooth movement", Orthod Craniofac Res. May 2009; 12(2):113-9. doi: 10.1111/j.1601-6343.2009.01444.x.
What Is Elastin? http://www.keracyte.com/index.php/site/page?view=whatIsElastin.
Wei et al., "Epicardial FSTL1 reconstitution regenerates the adult mammalian heart," Nature 525: 479-485 (Sep. 24, 2015).
Walsh & Choi "Biology of the RANK* RAN* OPG System in Immunity, Bone, and Beyond", Front Immunol. 2014; 5: 511.

Wagenseil et al., "Elastin in large artery stiffness and hypertension," Journal of Cardiovascular Translational Research, vol. 5, No. 3, 2012, pp. 264-273, Available online at < https://www.ncbi.nlm.nih.gov/pmc/articles/PMC3383658/ >, 21, pages.
W. Hoffmann, "Regeneration of the gastric mucosa and its glands from stem cells", Curr Med Chem, 15(29):3133-44 (2008).
Thattaliyath et al. "Modified Skeletal Myoblast Therapy For Cardiac Failure Using AAV SDF-1," Proc. Inti. Soc. Mag. Reson. Med. 16, p. 579 (2008).
Tamaki et al., "Cardiomyocyte Formation by Skeletal Muscle-Derived Multi-Myogenic Stem Cells after Transplantation into Infarcted Myocardium", PLoS ONE 3(3): e1789. doi:10.1371/journal.pone.0001789 (Mar. 2008).
Stenn et al., "Bioengineering the Hair Follicle," Organogenesis, 3(1): 6-13 (Jan.-Mar. 2007).
Stein et al., "The effect of transcutaneous electrical nerve stimulation on blood pressure," Blood Pressure, vol. 22, Issue 3, 2013, available online at < https://www.tandfonline.com/doi/full/10.3109/08037051.2012.722271 >, 5 pages.
Spadari et al., Electrical stimulation enhances tissue reorganization during orthodontic tooth movement in rats; Clinica Oral Investigations, Jan. 2017, vol. 21, Issue 1, pp. 111-120, Abstract.
Signature Orthodontics "Accelerated Tooth Movement", http://www.sigortho.com/accelerated-tooth-movement, visited Mar. 15, 2017.
Seifi & Jeszri "Correlation of bone resorption induced by orthodontic tooth movement and expression of RANKL in rats", Dental Journal, vol. 26, No. 4 (2009).
Schardong et al., "Intradialytic neuromuscular electrical stimulation reduces DNA damage in chronic kidney failure patients: a randomized controlled trial," Biomarkers, vol. 23, Issue 5, 2018, pp. 1-11.
Salcedo et al., "Low current electrical stimulation upregulates cytokine expression in the anal sphincter," Int. J. Colorectal Dis., Feb. 2012;27(2):221-5. doi: 10.1007/s00384-011-1324-3 Epub (Oct. 2011).
Sahoo and Losardo, "Exosomes and Cardiac Repair After Myocardial Infarction", Circulation Research, 114:333-344 (Jan. 16, 2014).
Robert Ferris, "Battle against baldness turns to stem cells" http://www.cnbc.com/2015/01/29/studies-indicate-its-possible-to-use-stem-cells-to-cure-baldness.html (Jan. 29, 2015).
Reversing Age-Related Hair Loss and Restoring Healthy Hair Growth in Men and Women https://nutritionreview.org/2015/08/reversing-age-related-hair-loss-and-restoring-healthy-hair-growth-in-men-and-women/ (Aug. 24, 2015).
R. Hamman "Modulation Of RANKL and Osteoprotegerin in Adolescents Using Orthodontic Forces", Masters Thesis, University of Tennessee (2010).
Prochazka et al., "Cocktail of Factors from Fat-derived Stem Cells Shows Promise for Critical Limb Ischemia" http://www.sciencenewsline.com/news/2016012204520017.html (Jan. 21, 2016).
Prochazka et al. "Therapeutic Potential of Adipose-Derived Therapeutic Factor Concentrate for Treating Critical Limb Ischemia," Cell Transplantation, 25(9), pp. 1623-1633(11) (2016).
Park et al. "Effects of SM-215 on Hair Growth by Hair Follicle Stimulation", Indian Journal of Science and Technology, vol. 8(25), DOI: 10.17485/ijst/2015/v8i25/80263, (Oct. 2015).
P. Banerjee "Electrical muscle stimulation for chronic heart failure: an alternative tool for exercise training?" Curr Heart Fail Rep., 7(2):52-8. doi: 10.1007/s11897-010-0013-9 (Jun. 2010).
Our Approach to Improve Hair Loss by Increasing Hair Growth Factor IGF-1, http://www.jhgc.com.sg/theory/igf-1/index.html.
Otero et al. "Expression and Presence of OPG and RANKL mRNA and Protein in Human Periodontal Ligament with Orthodontic Force", Gene-Regulation-and-Systems-Biology, 2016, 10, 15-20.
Nimeri et al. "Acceleration of tooth movement during orthodontic treatment—a frontier in Orthodontics", Prog Orthod 2013; 14:42; DOI: 10.1186/2196-1042-14-42.
Niiranen et al., "Relative Contributions of Arterial Stiffness and Hypertension to Cardiovascular Disease: The Framingham Heart Study," Journal of the American Heart Association, vol. 5, No. 11, 2016, 8 pages.
Mosteiro et al. "Tissue damage and senescence provide critical signals for cellular reprogramming in vivo." Science, 2016; 354 (6315): aaf4445 DOI: 10.1126/science.aaf4445.

(56) References Cited

OTHER PUBLICATIONS

Medtronic "Cardiac Resynchronization Therapy (CRT) Devices For Heart Failure" http://www.medtronic.com/us-en/patients/treatments-therapies/crt-devices.html.
Mass Device "Greatbatch wins FDA PMA for Algovita SCS" http://www.massdevice.com/greatbatch-wins-fda-pma-for-algovita-scs/ (Dec. 1, 2015).
Marie Ellis, "Cure for baldness? Stem cells bring hope" http://www.medicalnewstoday.com/articles/271898.php.
Li et al., "Exogenous IGF-1 promotes hair growth by stimulating cell proliferation and down regulating TGF-(Beta)1 in C57BL/6 mice in vivo" Growth Hormone & IGF Research, vol. 24, Issues 2-3, pp. 89-94 (Apr.-Jun. 2014).
Leonhardt's Launchpads Announces Filing of Patent for Bioelectric Stimulation Controlled Klotho Expression—Powerful Anti-aging and Regeneration Promoting Protein, by API PODDER, Published: Mar. 13, 2019, available online at < https://mysocialgoodnews.com/leonhardts-launchpads-announces-filing-of-patent-for-bioelectric-stimulation-controlled-klotho-expression-powerful-anti-aging-and-regeneration-promoting-protein/.
Kim et al., The effects of electrical current from a micro-electrical device on tooth movement, http://e-kjo.org/search_php?where=aview&id=10.4041/kjod.2008.38.5.337& . . . visited Aug. 2, 2017.
Khan et al. "Accelerating Tooth Movement: What Options We Have?" J Dent Health Oral Disord Ther 2016, 5(7): 00181.
Keles et al. "Inhibition of tooth movement by osteoprotegerin vs. pamidronate under conditions of constant orthodontic force", Eur J Oral Sci. Apr. 2007;115(2):131-6.
Kaur et al. "Electrically conductive polymers and composites for biomedical applications", RSC Adv., 2015,5, 37553-37567 DOI: 10.1039/C5RA01851J.
Kanzaki et al. "Periodontal ligament cells under mechanical stress induce osteoclastogenesis by receptor activator of nuclear factor kappaB ligand up-regulation via prostaglandin E2 synthesis", J Bone Miner Res 2002;17:21 / 220.
Kanzaki et al. "Local RANKL gene transfer to the periodontal tissue accelerates orthodontic tooth movement", Gene Therapy, (2006) 13, 678-685.
Kanzaki et al. "Local OPG gene transfer to periodontal tissue inhibits orthodontic tooth movement." J Dent Res 2004;83:92/ 925.
Kanno et al., Establishment of a Simple and Practical Procedure Applicable to Therapeutic Angiogenesis, Circulation, 1999, pp. 2682-2687, vol. 99.
K. Hart, Katherine A.nn D.D.S., "RANKL and Osteoprotegerin Levels in Response to Orthodontic Forces" (2012). Theses and Dissertations (ETD). Paper 107. http://dx.doi.org/10.21007/etd.cghs.2012.0127.
Jia et al., "Activin B Promotes Initiation and Development of Hair Follicles in Mice" Cells Tissues Organs, 198:318-326 (Feb. 2014).
Jansen et al. "Stimulation of osteogenic differentiation in human osteoprogenitor cells by pulsed electromagnetic fields: an in vitro study" BMC Musculoskeletal Disorders (2010) 11:188 DOI: 10.1186/1471-2474-11-188.
Israeli innovation uses nerve stimulation to treat heart failure https://www.israel21c.org/israeli-innovation-uses-nerve-stimulation-to-treat-heart-failure/ (Feb. 11, 2007).
Involvement of hepatocyte growth factor/scatter factor and Met receptor signaling in hair follicle morphogenesis and cycling, FASEB J Feb. 2000 14:319-332.
Anne Trafton, "A Noninvasive Method for Deep Brain Stimulation," MIT News Office, (available at http://news.mit.edu/2017/noninvasive-method-deep-brain-stimulation-0601), (Jun. 1, 2017), 3 pages.
Aydin et al., "Focusing of Electromagnetic Waves by a Left-Handed Metamaterial Flat Lens," vol. 13, (2005), pp. 8753-8759.
Barker et al., "A Formidable Foe is Sabotaging Your Results: What You Should Know About Biofilms and Wound Healing," Plastic and Reconstructive Surgery, vol. 139, (2017), p. 1184e-1194e.
Bioleohardnew, "Leonhardt Ventures Files Patent for Heart Valve Regeneration," (available at https://bioleonhardt.com/leonhardt-ventures-files-patent-for-heart-valve-regeneration/), (Mar. 20, 2018), 6 pages.
Borden et al., "Electric Current-Induced Detachment of *Staphylococcus epidermidis* Biofilms from Surgical Stainless Steel," Applied and Environmental Microbiology, vol. 70, (2004), pp. 6871-6874.
Cai et al., "Intermedin Inhibits Vascular Calcification by Increasing the Level of Matrix (Gamma)-Carboxyglutamic Acid Protein," Cardiovascular Research, vol. 85, (2010), pp. 864-873.
Canty et al., "Antibiotics Enhance Prevention and Eradication Efficacy of Cathodic-Voltage-Controlled Electrical Stimulation against Titanium-Associated Methicillin-Resistant *Staphylococcus aureus* and Pseudomonas aeruginosa Biofilms," mSphere, vol. 4, (May/Jun. 2019), e00178-19, 14 pages.
Caubet et al., "A Radio Frequency Electric Current Enhances Antibiotic Efficacy Against Bacterial Biofilms," Antimicrobial Agents and Chemotherapy, vol. 48, (2004), vol. 4662-4664.
Chen et al., "Deficiency in the Anti-Aging Gene Klotho Promotes Aortic Valve Fibrosis Through AMPK(Alpha)-Mediated Activation of RUNX2," Aging Cell, vol. 15, (Oct. 2016), pp. 853-860.
Chen et al., "The Role and Mechanism of (Alpha)-Klotho in the Calcification of Rat Aortic Vascular Smooth Muscle Cells," BioMed Research International, vol. 2015, (2015), 7 pages.
Chen et al., "The Strategy to Prevent and Regress the Vascular Calcification in Dialysis Patients," BioMed Research International, vol. 2017, (2017), 11 pages.
Chiang et al., "Silver-Palladium Surfaces Inhibit Biofilm Formation," Applied and Environmental Microbiology, vol. 75, (2009), pp. 1674-1678.
Costerton et al., "Mechanism of Electrical Enhancement of Efficacy of Antibiotics in Killing Biofilm Bacteria," Antimicrobial Agents and Chemotherapy, vol. 38, (1994), pp. 2803-2809.
Costerton et al., "The Application of Biofilm Science to the Study and Control of Chronic Bacterial Infections," The Journal of Clinical Investigation, vol. 112, (2003), pp. 1466-1477.
Delcaru et al., "Microbial Biofilms in Urinary Tract Infections and Prostatitis: Etiology, Pathogenicity, and Combating stralegies," Pathogens, vol. 5, (2016), 12 pages.
Ehrlich et al., "Engineering Approaches for the Detection and Control of Orthopaedic Biofilm Infections," Clinical Orthopaedics and Related Research, vol. 437, (2005), pp. 59-66.
Froughreyhani et al., "Effect of Electric Currents on Antibacterial Effect of Chlorhexidine Against Entrococcus Faecalis Biofilm: An in Vitro Study," Journal of Clinical and Experimental Dentistry, vol. 10, (Dec. 2018), pp. e1223-e1229.
Giladi et al., "Microbial Growth Inhibition by Alternating Electric Fields," Antimicrobial Agents and Chemotherapy, vol. 52, (2008), pp. 3517-3522.
Golberg et al., "Eradication of Multidrug-Resistant A. Baumannii in Burn Wounds by Antiseptic Pulsed Electric Field," Technology, vol. 2, (2014), pp. 153-160.
Golberg et al., "Pulsed Electric Fields For Burn Wound Disinfection in a Murine Model," Journal of Burn Care & Research, vol. 36, (2015), pp. 7-13.
Hari et al., "Application of Bioelectric Effect to Reduce the Antibiotic Resistance of Subgingival Plaque Biofilm: An in Vitro Study," Journal of Indian Society of Periodontology, vol. 22, (2018), pp. 133-139.
Harkens et al., "Chitosan-Cellulose Composite for Wound Dressing Material. Part 2. Antimicrobial Activity, Blood Absorption Ability, and Biocompatibility," Journal of Biomedical Materials Research Part B, Applied biomaterials, vol. 102, (2014), 1199-1206.
Hleonhardt, Leonhardt Announces Vibrational Energy Device For Preventing Blood Clots Provisional Patent Application and License Agreements, (available at https://leonhardtventures.com/leonhardt-announces-vibrational-energy-device-preventing-blood-clots-provisional-patent-application-license-agreements/), (Jul. 5, 2017), 5 pages.
https://www.dicardiology.com/content/bioleonhardt-unveils-stem-pump Jan. 28, 2014.
Istanbullu et al., "Electrochemical Biofilm Control: Mechanism of Action," Biofouling, vol. 28, (2012), pp. 769-778.

(56) References Cited

OTHER PUBLICATIONS

Kasimanickam et al., "Prevention and Treatment of Biofilms by Hybrid- and Nanotechnologies," International journal of Nanomedicine, vol. 8, (2013), pp. 2809-2819.

Kim et al., "Effect of Electrical Energy on the Efficacy of Biofilm Treatment Using the Bioelectric Effect," NPJ Biofilms and Microbiomes, vol. 1, (2015), Article 15016, 8 pages.

Kinney et al., "High Intensity Focused Electromagnetic Therapy Evaluated by Magnetic Resonance Imaging Safety and Efficacy Study of a Dual Tissue Effect Based Non-Invasive Abdominal Body Shaping," Lasers in Surgery and Medicine, vol. 51, (2019), pp. 40-46.

Lasserre et al., "Influence of Low Direct Electric Currents and Chlorhexidine Upon Human Dental Biofilms," Clinical and Experimental Dental Research, vol. 2, (Jul. 2016), pp. 146-154.

Lasserre et al., "Oral Microbes, Biofilms and Their Role in Periodontal and Peri-Implant Diseases," Materials, vol. 11, (Sep. 2018), Article 1802, 17 pages.

Lee et al. "Hepatocyte growth factor (HGF) activator expressed in hair follicles is involved in in vitro HGF-dependent hair follicle elongation," J. Dermatol. Sci., 25(2):156-63 (Feb. 2001).

Lee et al., "Targeted Release of Tobramycin From a pH-Responsive Grafted Bilayer Challenged With *S. aureus*," Biomacromolecules, vol. 16, (2015), pp. 650-659.

Lei et al., "Efficacy of Reversal of Aortic Calcification by Chelating Agents," Calcified Tissue International, vol. 93, (Nov. 2013), 15 pages.

Leibrock et al., "NH4CI Treatment Prevents Tissue Calcification in Klotho Deficiency," Journal of the American Society of Nephrology, vol. 26, (2015), pp. 2423-2433.

Lop et al., Cutting-Edge Regenerative Medicine Technologies for the Treatment of Heart Valve Calcification, Calcific Aortic Valve Disease, (2013), (available at http://dx.doi.org/10.5772/55327), 57 pages.

McLean et al., "Training the Biofilm Generation—a Tribute to J. W. Costerton," Journal of Bacteriology, vol. 194, (Dec. 2012), pp. 6706-6711.

Miles et al. "Assessment of the changes in arch perimeter and irregularity in the mandibular arch during initial alignment with the AcceleDent Aura appliance vs no appliance in adolescents: A single-blind randomized clinical trial", Dec. 2016, vol. 150, Issue 6 American Journal of Orthodontics and Dentofacial Orthopedics (9 pages).

Nodzo et al., "Cathodic Electrical Stimulation Combined With Vancomycin Enhances Treatment of Methicillin-Resistant *Staphylococcus aureus* Implant-Associated Infections," Clinical Orthopaedics and Related Research, vol. 473, (2015), pp. 2856-2864.

Nodzo et al., "Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), 1668-1675.

Novickij et al., "Induction of Different Sensitization Patterns of MRSA to Antibiotics Using Electroporation," Molecules, vol. 23,(2018), Article 1799, 10 pages.

O'Neill et al., "Recent Progress in the Treatment of Vascular Calcification," Kidney International, vol. 78, (Dec. 2010), pp. 1232-1239.

Palza et al., "Electroactive Smart Polymers for Biomedical Applications," Materials, vol. 12, (2019), 24 pages.

Plumbingtoday, "How to Remove Hard, White Mineral Deposits from Faucets/Showerheads," (available at https://plumbingtoday.biz/blog/how-to-remove-hard-white-mineral-deposits-from-faucets-showerheads), (Jul. 11, 2016), 4 pages.

Pozo et al., "Bioelectric Effect and Bacterial Biofilms. A Systematic Review," The International Journal of Artificial Organs, vol. 31, (2008), pp. 786-795.

Pozo et al., "Effect of Electrical Current on the Activities of Antimicrobial Agents Against Pseudomonas Aeruginosa, *Staphylococcus aureus*, and *Staphylococcus Epidermidis* Biofilms," Antimicrobial Agents and Chemotherapy, vol. 53, (2009), pp. 35-40.

Pozo et al., "Prevention of *Staphylococcus epidermidis* Biofilm Formation Using Electrical Current," Journal of Applied Biomaterials & Functional Materials, vol. 12, (2014), pp. 81-83.

Pozo et al., "The Electricidal Effect: Reduction of *Staphylococcus* and Pseudomonas Biofilms by Prolonged Exposure to Low-Intensity Electrical Current," Antimicrobial Agents and Chemotherapy, vol. 53, (2009), pp. 41-45.

Ren et al., "Efficient Eradication of Mature Pseudomonas Aeruginosa Biofilm via Controlled Delivery of Nitric Oxide Combined with Antimicrobial Peptide and Antibiotics," Frontiers in Microbiology, vol. 7, Article 1260, (Aug. 2016), 8 pages.

Roy et al., "Disposable Patterned Electroceutical Dressing (PED-10) Is Safe for Treatment of Open Clinical Chronic Wounds," Advances in Wound Care, vol. 8, (1019), pp. 149-159.

Sandvik et al., "Direct Electric Current Treatment under Physiologic Saline Conditions Kills *Staphylococcus epidermidis* Biofilms via Electrolytic Generation of Hypochlorous Acid," PloS one, vol. 8, (Feb. 2013), e55118, 14 pages.

Schmidt-Malan et al., "Activity of Fixed Direct Electrical Current in Experimental *Staphylococcus aureus* Foreign-Body Osteomyelitis," Diagnostic Microbiology and Infectious Disease, vol. 93, (2019), pp. 92-95.

Scott Jeffrey, "How to Decalcify Your Pineal Gland (And Why It's Really Important for Higher Mental Performance)," (available at https://scottjeffrey.com/decalcify-your-pineal-gland/). Retrieved on May 23, 2019, 23 pages.

Shahid et al., "Rhinosinusitis in Children," ISRN Otolaryngology, vol. 2012, Article ID 851831, (Dec. 2012), 11 pages.

Sharon M Moe, "Klotho: A Master Regulator of Cardiovascular Disease?," Circulation, vol. 125, (2012), pp. 2181-2183.

Shirtliff et al., "Assessment of the Ability of the Bioelectric Effect to Eliminate Mixed-Species Biofilms," Applied and Environmental Microbiology, vol. 71, (2005), pp. 6379-6382.

Shoji-Matsunaga et al. "Osteocyte regulation of orthodontic force-mediated tooth movement via RANKL expression." Scientific Reports, 7: 8753, published online Aug. 18, 2017, DOI:10 1038/s41598-017-09326-7.

Somayaji et al., "In Vitro Scanning Electron Microscopic Study on the Effect of Doxycycline and Vancomycin on Enterococcal Induced Biofilm," Iranian Endodontic Journal, vol. 5, (2010), pp. 53-58.

Souli et al., "Effects of Slime Produced by Clinical Isolates of Coagulase-Negative *Staphylococci* on Activities of Various Antimicrobial Agents," Antimicrobial Agents and Chemotherapy, vol. 42, (Apr. 1998), pp. 939-941.

Stewart et al., "Electrolytic Generation of Oxygen Partially Explains Electrical Enhancement of Tobramycin Efficacy Against Pseudomonas Aeruginosa Biofilm," Antimicrobial Agents and Chemotherapy, vol. 43, (1999), pp. 292-296.

Stoodley et al., "Influence of Electric Fields and pH on Biofilm Structure as Related to the Bioelectric Effect," Antimicrobial Agents and Chemotherapy, vol. 41, (1997), pp. 1876-1879.

Sultana et al., "Electrochemical Biofilm Control: A Review," Biofouling, vol. 31, (2015), pp. 745-758.

Szkotak Ei Al., "Differential Gene Expression to Investigate the Effects of Low-Level Electrochemical Currents on Bacillus subtilis," AMB Express, vol. 1, (Nov. 2011), 12 pages.

Vinod Krishnan, Ze'ev Davidovitch (eds.), Biological Mechanisms of Tooth Movement, (John Wiley & Sons 2015 (10 Pages).

Wang et al., "Controlling *Streptococcus mutans* and *Staphylococcus aureus* Biofilms With Direct Current and Chlorhexidine," AMB Express, vol. 7, (Nov. 2017), 9 pages.

Wellman et al., "Bacterial Biofilms and the Bioelectric Effect," Antimicrobial Agents and Chemotherapy, vol. 40, (1996), pp. 2012-2014.

Wong et al., "Dual Functional Polyelectrolyte Multilayer Coatings for Implants: Permanent Microbicidal Base With Controlled Release of Therapeutic Agents," Journal of the American Chemical Society, vol. 132, (2010), p. 17840-17848.

Wu et al., "Vascular Calcification: an Update on Mechanisms and Challenges in Treatment," Calcified Tissue International, vol. 93, (Oct. 2013), pp. 365-373.

(56) References Cited

OTHER PUBLICATIONS

Yang Lei, "Mechanisms and Reversal of Elastin Specific Medial Arterial Calcification" (2014). All Dissertations, Paper 1307, (available at https://tigerprints.clemson.edu/all_dissertations/1307), 214 pages.

Yarbrough et al., "Specific Binding and Mineralization of Calcified Surfaces by Small Peptides," Calcified Tissue International, vol. 86, (2010), pp. 58-66.

Zalavras, Charalampos G. "CORR Insights(Registered): Cathodic Voltage-Controlled Electrical Stimulation Plus Prolonged Vancomycin Reduce Bacterial Burden of a Titanium Implant-associated Infection in a Rodent Model," Clinical Orthopaedics and Related Research, vol. 474, (2016), pp. 1676-1678.

Zhang et al., "Highly Stable and Reusable Imprinted Artificial Antibody Used for in Situ Detection and Disinfection of Pathogens," Chemical Science, vol. 6, (2015), pp. 2822-2826.

Brooks et al. "Bioelectric impedance predicts total body water, blood pressure, and heart rate during hemodialysis in children and adolescents" J. Ren Nutr., 18(3):304-311 (May 2008); doi: 10.1053/j.jrn.2007.11.008.

Collins "Bioelectric Signals Can Be Used to Detect Early Cancer," Tufts News, http://now.tufts.edu/news-releases/bioelectric-signals-used-detect-early-cancer (Feb. 1, 2013).

Fatemi et al. "Imaging elastic properties of biological tissues by low-frequency harmonic vibration" Proceedings of the IEEE, 91 (10):1503-1519 (Oct. 2003).

Guimarães-Camboa et al. "Redox Paradox: Can Hypoxia Heal Ischemic Hearts?" Cell, 39(4):392-394, (Nov. 21, 2016) DOI: http://dx.doi.org/10.1016/j.devcel.2016.11.007.

Huang et al. "Myocardial transfection of hypoxia-inducible factor-1a and co-transplantation of mesenchymal stem cells enhance cardiac repair in rats with experimental myocardial infarction", Stem Cell Research & Therapy 5:22 (2014) DOI: 10.1186/scrt410.

International Search Report for International Application No. PCT/US19/52288, dated Jan. 10, 2020, 11 pages.

International Written Opinion for International Application No. PCT/US19/52288, dated Jan. 10, 2020, 07 pages.

Kido et al. "Hypoxia-Inducible Factor 1-Alpha Reduces Infarction and Attenuates Progression of Cardiac Dysfunction After Myocardial Infarction in the Mouse" JACC, vol. 46, Issue 11, Dec. 6, 2005, pp. 2116-2124. https://doi.org/10.1016/j.jacc.2005.08.045.

Pierce et al. "Collection and characterization of amniotic fluid from scheduled C-section deliveries," Cell Tissue Bank, DOI 10.1007/s10561-016-9572-7 (Springer, 2012) and is available from Irvine Scientific.

Tajima et al. "HIF-1alpha is necessary to support gluconeogenesis during liver regeneration" Biochem Biophys Res Commun. Oct. 2, 2009; 387(4):789-94. doi: 10.1016/j.bbrc.2009 07.115. Epub Jul. 28, 2009.

Aubert et al. "A new ultrasonic process for a renewal of aortic valve decalcification" Cardiovascular Ultrasound 2006, 4:2 doi:10.1186/1476-7120-4-2.

Back et al. "Endogenous Calcification Inhibitors in the Prevention of Vascular Calcification: A Consensus Statement From the COST Action EuroSoftCalcNet" Frontiers in Cardiovascular Medicine | www.frontiersin.org, Jan. 2019 vol. 5 | Article 196.

Chen et al. "Secreted Klotho Attenuates Inflammation-Associated Aortic Valve Fibrosis in Senescence-Accelerated Mice P1" Hypertension. 2018;71:877-885. DOI: 10.1161/HYPERTENSIONAHA.117.10560.) Downloaded from http://ahajournals.org by on Apr. 24, 2020 (9 pages).

Dietrich et al. "Decalcification of the mitral annulus: surgical experience in 81 patients" Thorac Cardiovasc Surg. Oct. 2006;54(7):464-7 (Abstract Only).

Heart Valve Calcifications-Focused Ultrasound TherapyFocused Ultrasound Therapy; Research Paper Last Updated Jan. 28, 2020, The Focused Ultrasound Foundation Newsletter (5 pages).

Hu et al. "Klotho Deficiency Causes Vascular Calcification in Chronic Kidney Disease" J Am Soc Nephrol. Jan. 22, 2011(1): 124-136.

King et al. "Mechanical Decalcification of the Aortic Valve" 272 The Annals of Thoracic Surgery vol. 42 No. 3 Sep. 1986 (pp. 269-272).

Kose et al. "Citric acid as a decalcifying agent for the excised calcified human heart valves" Anadolu Kardiyol Derg 2008; 8: 94-8 (Eng Abstract).

Malakhov et al. "Assessment of Efficacy of Non-Invasive Peripheral Transcutaneous Electrical Nerve Stimulation for Correction of Blood Pressure in Patients With Arterial Hypertension" Journal of Hypertension: Jul. 2019—vol. 37—Issue—p. e88-e89 doi: 10.1097/01.hjh.0000570296.70620.44.

McBride et al. "Aortic valve decalcification" J Thorac Cardiovasc Surg. Jul. 1990;100(1):36-42; discussion 42-3 (Abstract Only).

Price et al. "Mitral Valve Repair is Feasible Following Extensive Decalcification and Reconstruction of the Atrioventricular Groove" J Heart Valve Dis. Jan. 2015;24(1):46-52 (Abstract Only).

Tavlasoglu et al. "Is partial decalcification of posterior mitral annular bed logical in all mitral valve replacement procedures?" European Journal of Cardio-Thoracic Surgery 43 (2013) 449-450.

Totsugawa, et al. "Ultrasonic annular debridement in minimally invasive aortic valve replacement" Gen Thorac Cardiovasc Surg. Jan. 2020;68(1):81-83. doi: 10.1007/s11748-019-01158-8. Epub Jun. 15, 2019. (Abstract Only).

Valvublator Heart Valve Regeneration, accessed Apr. 24, 2020 https://valvublator.com (6 pages).

Alghatrif et al. "The Conundrum of Arterial Sliffness, Elevated blood pressure, and Aging" Curr Hypertens Rep. Feb. 2015; 17(2): 12. doi: 10.1007/s11906-014-0523-z.

Beitelshees et al. "CXCL5 polymorphisms are associated with variable blood pressure in cardiovascular disease-free adults" Hum Genomics. 2012; 6(1): 9.

Cowburn et al. "HIF isoforms in the skin differentially regulate systemic arterial pressure" Proc Natl Acad Sci U S A. Oct. 22, 2013; 110(43): 17570-17575.

Greenwald "Pulse pressure and arterial elasticity" QJM: An International Journal of Medicine, vol. 95, Issue 2, 2002, pp. 107-112.

Leonhardt "Leonhardt Adds HIF-1 Alpha To Estate of Bioelectric Controlled Release Regenerative Proteins" Press Release, Published Jun. 13, 2017.

Li "Regulation of Renal Oxygenation and Blood Pressure" Art. Virginia Commonwealth University, Richmond, VA, United States (Abstract).

Longhurst et al. "Evidence-based blood pressure reducing actions of electroacupuncture: mechanisms and clinical application" Sheng Li Xue Bao. Oct. 25, 2017; 69(5): 587-597.

Nordstorm "Electrical Stimulation Blood Pressure Treatment Devices Market to Set Astonishing Growth by 2026" Art. Apr. 4, 2019 Gator Ledger.

Sethi et al. "Aortic stiffness: pathophysiology, clinical implications, and approach to treatment" Integr Blood Press Control. 2014; 7: 29-34.

Spiridonov et al. "Effect of Transcutaneous Electrical Stimulation of Nerves on Blood Pressure and Blood Content of Neuropeptide CGRP and Nitric Oxide in Hypertensive Rats with Metabolic Disturbances" Bull Exp Biol Med (Feb. 2019) 166: 436-437.

Warner"Inflammation Adds to Blood Pressure Risks, High Blood Pressure and C-Reactive Protein May Trigger Heart Attack, Stroke" Art. WebMD Health News (2003) 2 pages.

Welch "RGS2 Proteins Regulate Blood Pressure" JASN Nov. 2010, 21 (11) 1809-1810.

Yu et al. "Association between inflammation and systolic blood pressure in RA compared to patients without RA" Arthritis Research & Therapy vol. 20, Article No. 107 (2018).

Interesting study about prolactin, VEGF and angiogenic inhibition, http://www.regrowth.com/hair-loss-forums/topic/interesting-study-about-prolactin-vegf-and-angiogenic-inhibition/ (Nov. 2006).

Hy et al., "Insulin-like growth factor 1 and hair growth," Dermatol Online J,; 5(2):1 (Nov. 1999).

HU Klein, "Vagus Nerve Stimulation: A new approach to reduce heart failure" Cardiology Journal (2010).

Hopkins Medicine "Overview of Pacemakers and Implantable Cardioverter Defibrillators (ICDs)," hopkinsmedicine.org/healthlibrary/

(56) References Cited

OTHER PUBLICATIONS conditions/cardiovascular_diseases/ )verview of pacemakers and implantable cardioverter defibrillators icds 85,P00234/, last visited Sep. 12, 2018.
Holding et al. "The correlation of RANK, RANKL and TNFa expression with bone loss volume and polyethylene wear debris around hip implants" Biomaterials 27(30):5212-9—Nov. 2006.
HN Sabbah "Electrical vagus nerve stimulation for the treatment of chronic heart failure", Cleve Clin J Med, 78 Suppl 1: S24-9. doi: 10.3949/ccjm.78.s1.04 (Aug. 2011).
Hearts build new muscle with this simple protein patch, jacobsschool.ucsd.edu/news/news_releases/release.sfe?id=1813(Sep. 16, 2015).
Hair Growth Factors, Nanogen, http://www.svijet-kose.com/dokumenti/Serum-vegf.pdf.
Giganti et al. "Changes in serum levels of TNF-alpha, IL-6, OPG, RANKL and their correlation with radiographic and clinical assessment in fragility fractures and high energy fractures", J Biol Regul Homeost Agents, Oct.-Dec. 2012; 26 (4):671-80.
Fukuoka et al., "The Latest Advance in Hair Regeneration Therapy Using Proteins Secreted by Adipose-Derived Stem Cells" The American Journal of Cosmetic Surgery, 29(4):273-282 (2012).
Fukuoka and Suga, "Hair Regeneration Treatment Using Adipose-Derived Stem Cell Conditioned Medium: Follow-up With Trichograms" Eplasty, 15:e10 (Mar. 2015).
FDA Approves Algovita Spinal Cord Stimulation System from Greatbatch, http://www.odtmag.com/contents/view_breaking-news/2015-12-02/fda-approves-algovita-spinal-cord-stimulation-system-from-greatbatch (Dec. 2, 2015).
Electrical brain stimulation could support stroke recovery https://www.sciencedaily.com/releases/2016/03/160316151108.htm (Mar. 16, 2016).
Electric Tumor Treatment Fields, No. 0827 Policy, http://www.aetna.com/cpb/medical/data/800_899/0827.html (Nov. 18, 2016).
Elastatropin(Registered) in Scalp & Hair Conditioning https://www.proteingenomics.com/haircare.html.
Dong-Hwan Kim et al., The effects of electrical current from a micro-electrical device on tooth movement, Korean Orthod., Oct. 2008, 38(5):337-346.
Dibart et al. "Tissue response during Piezocision-assisted tooth movement: a histological study in rats", Eur J Orthod (2014) 36 (4): 457-464; DOI: https://doi.org/10.1093/ejo/cjt079.
D. Grad, "Electrical Scalp Device Can Slow Progression of Deadly Brain Tumors", New York Times, https://www.nytimes.com/2014/11/16/health/electrical-scalp-device-can-slow-progression-of-deadly-brain-tumors.html?_r=0 (Nov. 15, 2014).
D'Apuzzo et al. "Biomarkers of Periodontal Tissue Remodeling during Orthodontic Tooth Movement in Mice and Men Overview and Clinical Relevance", The Scientific World Journal, vol. 2013 (2013), Article ID 105873, 8 pages, http://dx.doi org/10.1155/2013/105873.
Control of pelage hair follicle development and cycling by complex interactions between follistatin and activin, FASEB J (Jan. 2, 2003).
Control of Hair Growth by a Growth Factor Protein, http://www.hairloss-reversible.com/control-of-hair-growth-by-a-growth-factor-protein/.
Columbia "Implant Procedure Concepts—Pacemaker, ICD and CRT Overview," columbia.edu/itc/hs/medical/hickey/docs/Pacemaker,%20ICD%20and%20CRT%20overview%20022007.pdf, last risited Sep. 12, 2018.
Chen et al., "Regenerative Hair Waves in Aging Mice and Extra-Follicular Modulators Follistatin, Dkk1, and Sfrp4," Journal of Investigative Dermatology, Aug. 2014, vol. 134, Issue 8, pp. 2086-2096.
Chemet & Levin, "Transmembrane voltage potential is an essential cellular parameter for the detection and control of tumor development in a Xenopus model," Dis. Models & Mech. 6, pp. 595-607 (2013); doi:10.1242/dmm.010835.
Chang et al. Effect of Pulse-Burst Electromagnetic Field Stimulation on Osteoblast Cell Activities; Bioelectromagnetics 25:457-465 (2004).
Chang et al. "Pulsed electromagnetic fields stimulation affects osteoclast formation by modulation of osteoprotegerin, RANK ligand and macrophage colony-stimulating factor", Journal of Orthopaedic Research, 23 (2005) 1308-1314.
Cerrada et al. "Hypoxia-Inducible Factor 1 Alpha Contributes to Cardiac Healing in Mesenchymal Stem Cells-Mediated Cardiac Repair," Stem Cells and Development, 22(3): 501-511 (2013).
Bradshaw et al. "Designer self-assembling hydrogel scaffolds can impact skin cell proliferation and migration" Nature Scientific Reports, vol. 4, Article No. 6903 (2014).
Blood Vessels Hold Key To Thicker Hair Growth, https://www.sciencedaily.com/releases/2001/02/010215074636.htm(Feb. 2001).
Bio-Leonhardt "Micro Stimulator" http://www.bioleonhardt.com/micro-stimulator/.
Barbault et al., Amplitude-modulated electromagnetic fields for the treatment of cancer: Discovery of tumor-specific frequencies and assessment of a novel therapeutic approach, Journal of Experimental & Clinical Cancer Research, Apr. 14, 2009, vol. 28, No. 51, doi:10.1186/1756-9966-28-51, 10 pages.
B. Borgobello "FDA approves the treatment of brain tumors with electrical fields," New Atlas, http://newatlas.com/treatment-of-brain-tumors-with-electrical-fields/21433/(Feb. 13, 2012), last visited Sep. 12, 2018.
Apuzzo et al. "Biomarkers of Periodontal Tissue Remodeling during Orthodontic Tooth Movement in Mice and Men Overview and Clinical Relevance", The Scientific World Journal, vol. 2013 (2013), Article ID 105873, 8 pages, http://dx.doi.0rg/10.1155/2013/105873.
Almpani et al., "Nonsurgical Methods for the Acceleration of the Orthodontic Tooth Movement", Tooth Movement. Front Oral Biol., vol. 18, pp. 80-91 (Karger, Basel, CH 2016) (DOI: 10.1159/000382048), Published online: Nov. 24, 2015.
Alice Park, "Shrinking Stem Cells Are the Real Reason for Hair Loss" Time, (Feb. 5, 2016).
Abstract of Zhang et al., "Comparison of arterial stiffness in non-hypertensive and hypertensive population of various age groups," Jan. 24, 2018, 2 pages.
Abstract of Sabino-Carvalho et al., "Non-invasive Vagus Nerve Stimulation Acutely Improves Blood Pressure Control in a Placebo Controlled Study," The FASEB Journal, vol. 31, 2017, available online at < https://www.fasebj.org/doi/abs/10.1096/fasebj.31.1_supplement.848.8 >, 2 pages.
Abstract of Collette et al., "Measurement of the local aortic stiffness by a non-invasive bioelectrical impedance technique," in Medical & Biological Engineering, vol. 49, No. 4, Feb. 2011, pp. 431-439, Available online at < https://www.ncbi.nlm.nih.gov/pubmed/21286830>, 1 page.
"FDA Approves Algovita Spinal Cord Stimulation System from Greatbatch," http://www.odtmag.com/contents/view_breaking-news/2015-12-02/fda-approves-algovita-spinal-cord-stimulation-jystem-from-greatbatch (Dec. 2, 2015).
"Electrical brain stimulation could support stroke recovery," sciencedaily.com/releases/2016/03/160316151108.htm (Mar. 16,2016), last visited Sep. 12, 2018.
"Electric Tumor Treatment Fields," No. 0827 Policy, aetna.com/cpb/medical/data/800_899/0827.html (Nov. 18, 2016), last visited Sep. 12, 2018.
Apuzzo et al. "Biomarkers of Periodontal Tissue Remodeling during Orthodontic Tooth Movement in Mice and Men Overview and Clinical Relevance", The Scientific World Journal, vol. 2013 (2013), Article ID 105873, 8 pages, http://dx.doi org/10.1155/2013/105873.
Beebe et al. "Bioelectric Applications for Treatment of Melanoma," Cancers (Basel). Sep. 2010; 2(3): 1731-1770, published online Sep. 27, 2010; doi: 10.3390/cancers20317.
Campbell Et Ali. "Electrical stimulation to optimize cardioprotective exosomes from cardiac stem cells" Med Hypotheses. Mar. 2016; 88:6-9. doi: 10.1016/j.mehy.2015.12.022. Epub Jan. 11, 2016.
Cervera "The interplay between genetic and bioelectrical signaling permits a spatial regionalisation of membrane potentials in model multicellular ensembles," Nature, Scientific Reports, Oct. 12, 2016 vol. 6, Article No. 35201 (2016).
Ciria et al., Antitumor effectiveness of different amounts of electrical charge in Ehrlich and fibrosarcoma Sa-37 tumors, BMC Cancer, Nov. 26, 2004, 10 pages, vol. 4, No. 87.

(56) References Cited

OTHER PUBLICATIONS

Dai et al. "Nanosecond Pulsed Electric Fields Enhance the Antitumour Effects of the mTOR Inhibitor Everolimus against Melanoma," Scientific Reports vol. 7, Article No. 39597 (2017).
Hamzelou et al. "Cancer reversed in frogs by hacking cells' electricity with light," New Scientist This Week, Mar. 16, 2016.
Jing-Hong et al. "Electrochemical Therapy of Tumors" Hindawi Publishing Corporation, Conference Papers in Medicine, vol. 2013, Article ID 858319, 13 pages, http://dx.doi.org/10.1155/2013/858319.
Keunen et al. "Anti-VEGF treatment reduces blood supply and increases tumor cell invasion in glioblastoma," Proc. Natl. Acad. Sci. U. S. A. Mar. 1, 2011; 108(9): 3749-3754, published online Feb. 14, 2011; doi: 10.1073/pnas.1014480108.
Lanzetto et al. "Fundamental principles of an anti-VEGF treatment regimen: optimal application of intravitreal anti-vascular endothelial growth factor therapy of macular diseases," Graefes Arch. Clin. Exp. Ophthalmol. 2017; 255(7): 1259-1273 (published online May 19, 2017); doi: 10.1007/s00417-017-3647-4.
Meadows et al. "Anti-VEGF Therapies in the Clinic," Cold Spring Harb. Perspect. Med. Oct. 2012; 2(10): a006577: doi: 10.1101/cshperspect.a006577.
Mishra "Angiogenic neovessels promote tissue hypoxia," Proc. Natl. Acad. Sci. U. S. A. Sep. 20, 2016; 113(38): 10458-10460, published online Sep. 1, 20163; doi: 10 1073/pnas.1612427113.
Pupo et al.. Electrotherapy on Cancer: Experiment and Mathematical Modeling, Current Cancer Treatment—Novel Beyond Conventional Approaches, Prof. Oner Ozdemir (Ed.) ISBN: 978-953-307-397-2, InTech, Available from http://www.intechopen.com/books/current-cancer-treatment-novel-beyond-conventional-approaches/electrotherapy-on-cancer-experiment-and-mathematical-modeling, 2011.
Puro et al "Bioelectric impact of pathological angiogenesis on vascular function," PNAS Aug. 30, 2016 113 (35) 9934-9939; published ahead of print Aug. 22, 2016 https://doi.org/10.1073/pnas.1604757113.
RFA (radiofrequency ablation), Swedish Medical Imaging, 2 pages, author unknown, undated.
Silvers et al. "The Bioelectric Code: Reprogramming Cancer and Aging from the Interface of Mechanical and Chemical Microenvironments," Front. Cell Dev. Biol., Mar. 6, 2018; doi.org/10.3389/fcell.2018.00021.
Abdel-Rehim "Change of serum klotho protein and its relationship with endothelial dysfunction, oxidative stress and arterial aging in essential hypertensive patients" J Kidney 2018, vol. 4 (Dec. 2018).
Ahrens et al. "Klotho expression is a prerequisite for proper muscle stem cell function and regeneration of skeletal muscle" Ahrens et al. Skeletal Muscle (Jul. 2018) 8:20 pp. 1-14.
Akbari et al. "Association of Klotho gene polymorphism with hypertension and coronary artery disease in an Iranian population" BMC Cardiovascular Disorders (Dec. 2018) 18:237.
Carboni et al. "An initial study on the effect of functional electrical stimulation in erectile dysfunction: a randomized controlled trial" IJIR: Your Sexual Medicine Journal (May 2018) 30:97-101.
Chaikin et al. "Microcurrent stimulation in the treatment of dry and wet macular degeneration" Clinical Ophthalmology 2015:9 2345-2353 (Dec. 2015).
Jamal et al. "Klotho, Hypertension and Arterial Stiffness: A Review" Austin J Nephrol Hypertens.(Jul. 2019) 6(2): 1082.
JCCR "Emerging roles of klotho in cardiovascular diseases%5D" Accessed Jun. 2, 2021 https://medcraveonline.com/JCCR/emerging-roles-of-klotho-in-cardiovascular-diseases.html%5D.
Kawagishi et al. S"onic hedgehog signaling regulates the mammalian cardiac regenerative response" Journal of Molecular and Cellular Cardiology; vol. 123, p. 180-184 (Oct. 2018).
Leonhardt "PressureStim Blood Pressure Control" accessed Jun. 2, 2021, https://pressurestim.com.
Leonhardt "PressureStim Receives IRB Approval to Launch Bioelectric Hypertension Treatment Clinical Study" Accessed Jun. 2, 2021, https://www.prdistribution.com/news/pressurestim-receives-irb-approval-to-launch-bioelectric-hypertension-treatment-clinical-study-2.html?fbclid=IwAR28Dh97RAKXXHrfgUONKW1pk-MWyeF_ibUlpQc_2XEN32C6sS%E2%80%A6.
Maltese et al. "The Putative Role of the Antiageing Protein Klotho in Cardiovascular and Renal Disease" Hindawi Publishing Corporation International Journal of Hypertension, (Sep. 2011) vol. 2012, Article ID 757469, 5 pages.
McMillan "Longevity Protein Enables Muscle Regeneration In Old Mice" accesses Jun. 2, 2021 https://www.forbes.com/sites/fionamcmillan/2018/11/25/longevity-protein-enables-muscle-regeneration-in-old-mice/? sh=51709d57392a.
Ronchetti et al. "Dermal alterations in patients with Wilson's disease treated with D-penicillamine" J Submicrosc Cytol Pathol (Jan. 1989) 21(1):131-9.
Santos et al. "Interferential electrical stimulation improves peripheral vasodilatation in healthy individuals" Braz J Phys Ther. May-Jun. 2013; 17(3):281-288.
Sartori et al. "Effects of Transcutaneous Electrical Nerve Stimulation in Autonomic Nervous System of Hypertensive Patients: A Randomized Controlled Trial" Current Hypertension Reviews, Apr. 2018, 14, 66-71.
Su et al. "Klotho protein lowered in elderly hypertension" Int J Clin Exp Med (Aug. 2014) 7(8):2347-2350.
Sun "Regulation of Blood Pressure by Klotho" University of Oklahoma Health Sciences Center, Oklahoma City, OK, United States; accessed Jun. 2, 2021; https://grantome.com/grant/NIH/R01-HL102074-01A1.
Takenaka et al. "Klotho Supplementation Attenuatesblood Pressure and Cyst Growth Inmouse Polycystic Kidney Disease" Journal of Hypertension: vol. 36—Issue—p. e76 (Jun. 2018).
Zhou et al. "Klotho Ameliorates Kidney Injury and Fibrosis and Normalizes Blood Pressure by Targeting the Renin-Angiotensin System" The American Journal of Pathology, vol. 185, No. 12, Dec. 2015.
Zhou et al. "Klotho Gene Deficiency Causes Salt-Sensitive Hypertension via Monocyte Chemotactic Protein-1/CC Chemokine Receptor 2-Mediated inflammation" J Am Soc Nephrol 26: 121-132, 2015 (Accepted Apr. 2014).
Blum "Role of cytokines in heart failure," American Heart Journal, vol. 135, Issue 2, Feb. 1998, pp. 181-186; doi.org/10.1016/S0002-8703(98)70080-8.
Corrigan et al. "Neurogenic inflammation after traumatic brain injury and its potentiation of classical inflammation", Journal of Neuroinflammation, 2016, 13:264; doi://doi.org/10.1186/s12974-016-0738-9.
Deswal et al. "Cytokines and Cytokine Receptors in Advanced Heart Failure An Analysis of the Cytokine Database from the Vesnarinone Trial (VEST)," Circulation. 2001;103:2055-2059; ://doi.org/10.1161/01.CIR.103.16.2055.
Gavira et al. "Repeated implantation of skeletal myoblast in a swine model of chronic myocardial infarction," Eur. Heart J., 31(8): 1013-1021. doi: 10.1093/eurheartj/ehp342 (2010).
Gullestad et al. "Inflammatory cytokines in heart failure: mediators and markers," Cardiology. 2012;122(1):23-35. doi: 10.1159/000338166. Epub Jun. 12, 2012.
Liesz et al. "Editorial: Mechanisms of neuroinflammation and inflammatory neurodegeneration in acute brain injury" Front Cell. Neurosci., 2015 doi://doi.org/10.3389/fncel.2015.00300.
Lobo-Silva et al. "Balancing the immune response in the brain: IL-10 and its regulation," Journal of Neuroinflammation, 13:297 (2016); doi.org/10.1186/s12974-016-0763-8.
Mann, "Innate Immunity and the Failing Heart: The Cytokine Hypothesis Revisited," Circ. Res. Mar. 27, 2015; 116(7): 1254-1268.
Matsumori, "Cytokines and Heart Failure: Pathophysiological Roles and Therapeutic Implications," Heart Failure, Springer, Tokyo; doi.org/10.1007/978-4-431-68331-5_3.
Paulus "Cytokines and heart failure," Heart Fail. Monit. 2000; 1(2):50-6.
Schimmel et al. "Neuroinflammation in traumatic brain injury: A chronic response to an acute injury" Brain Circ, 2017, 3(3): 135-142.

(56) References Cited

OTHER PUBLICATIONS

Ueland et al. "Inflammatory cytokines as biomarkers in heart failure," Clinica Chimica Acta, vol. 443, Mar. 30, 2015, pp. 71-77; doi.org/10.1016/j.cca.2014.09.001.
Xiong et al. "Current understanding of neuroinflammation after traumatic brain injury and cell-based therapeutic opportunities" Chin J Traumatol. Jun. 2018; 21(3): 137-151. doi: 10.1016/j.cjtee. 2018.02.003.
Zdzisinska et al. "RANK/RANKL i OPG w szpiczaku plazmocytowym [The role of RANK/RANKL and OPG in multiple myeloma]" Postepy Hig Med Dosw (Online). 2006; 60:471-482 (Abstract Only).
Zhao et al. "Local osteoprotegerin gene transfer inhibits relapse of orthodontic tooth movement." Am J Orthod Dentofacial Orthop. Jan. 2012; 141(1):30-40. doi: 10.1016/j.ajodo.2011.06.035.
Andersson et al. "Drinking, antidiuresis and milk ejection from electrical stimulation within the hypothalamus of the goat," Acta Physiol Scand. Dec. 31, 1955; 35(2): 191-201; DOI: 10.1111/j.1748-1716.1955.tb01277.x.
Ando et al." RANKL/RANK/OPG: key therapeutic target in bone oncology" Curr Drug Discov Technol. Sep. 5, 2008(3): 263-268.
Aronowitz et al. "Mechanical versus enzymatic isolation of stromal vascular fraction cells from adipose tissue" SpringerPlus (2015) 4:713 DOI 10.1186/s40064-015-1509-2.
Atkinson et al. "Bioelectric Properties of the Tooth" 1969 vol. 48 issue: 5, pp. 789-794.
Berman "Suzanne Somers' Experimental Breast Reconstruction" Medpage Today, Feb. 7, 2012, www.medpagetoday.com > blogs > celebritydiagnosis.
Bi et al. "Key Triggers of Osteoclast-Related Diseases and Available Strategies for Targeted Therapies: A Review" Front Med (Lausanne). 2017; 4: 234. doi: 0.3389/fmed.2017.00234.
Boyle "Wound-Treating Jelly Regenerates Fresh, Scar-Free Skin", Popular Science, (Dec. 15, 2011), "New material developed for accelerated skin regeneration in major wounds", Science Highlight, (National Institute of Biomedical 11Imaging and Bioengineering, Dec. 17, 2015).
Buckle et al. "Soluble Rank Ligand Produced by Myeloma Cells Causes Generalised Bone Loss in Multiple Myeloma" PLoS One. 2012; 7(8): e41127. doi: 10.1371/journal.pone.0041127 PMCID: PMC3430669.
CalXStars Business Accelerator, Inc.—Website—Justia Patents—Mar. 15, 2017—US Patent Application for Stimulator, Pump & Composition Patent Application (Application #20170266371) https://protect-us.mimecast.com/s/tSaBCxkVlwuDr61CvMWbF?domain=patents.justia.com.
Christouls et al. "Pathogenesis and Management of Myeloma Bone Disease" Expert Rev Hematol. 2009 2(4):385-398.
Cross et al. "Milk Ejection following Electrical Stimulation of the Pituitary Stalk in Rabbits," Nature 166, 994-995 (Dec. 9, 1950); doi: 10.1038/166994b0 (Abstract Only).
El-Bialy et al. "Effect of Low Intensity Pulsed Ultrasound (LIPUS) on Tooth Movement and Root Resorption: A Prospective Multi-Center Randomized Controlled Trial" J. Clin. Med. 2020, 9, 804; doi:10.3390/jcm9030804.
Ferrucci, D. A. "Introduction to This is Watson," in IBM Journal of Research and Development, vol. 56, No. 3.4, p. 1:1-1:15, May-Jun. 2012. DOI: 10.1147/JRD.2012.2184356.
Fili et al. "Therapeutic implications of osteoprotegerin" Cancer Cell International vol. 9, Article No. 26 (2009).
Fonseca et al. "Electrical stimulation: Complementary therapy to improve the performance of grafts in bone defects?" Journal of Biomedical Materials Research Part B: Applied Biomaterials 2018 vol. 000b, Issue 0.
Goranov et al. "Bone Lesions in Multiple Myeloma—The OPG/RANK-ligand System" Folia Med (Plovdiv). 2004; 46(3): 5-11 (Abstract Only).
Goswami et al. "Osteoprotegerin rich tumor microenvironment: implications in breast cancer" Oncotarget. Jul. 5, 2016; 7(27): 42777-42791.

Gurbax et al. "Accelerated Orthodontic Tooth Movement: A Review" mod Res Dent. 1(2). MRD.000508. 2017. DOI: 10.31031/MRD. 2017.01.000508.
Holen et al. "Role of Osteoprotegerin (OPG) in Cancer" Clin Sci (Lond). Mar. 2006; 110(3):279-91. doi: 10.1042/CS20050175.
Hu et al. "Exosomes derived from human adipose mesenchymal stem cells accelerates cutaneous wound healing via optimizing the characteristics of fibroblasts", Nature Scientific Reports, vol. 6, Article No. 32993 (2016).
Hudson et al. "Local delivery of recombinant osteoprotegerin enhances postorthodontic tooth stability" Calcif Tissue Int. Apr. 2012; 90(4):330-42. doi: 10.1007/S00223-012-9579-4.
Iglesias-Linares et al. "The use of gene therapy vs. corticotomy surgery in accelerating orthodontic tooth movement " Orthod Craniofac Res. Aug. 2011; 14(3):138-48. doi: 10.1111/j.1601-6343.2011.01519. x.
Infante et al. "RANKL/RANK/OPG system beyond bone remodeling: involvement in breast cancer and clinical perspectives" Journal of Experimental & Clinical Cancer Research (2019) 38:12. https://doi.org/10.1186/s13046-018-1001-2.
International Search Report for International Application No. PCT/US2019/025177, dated Sep. 3, 2019, 3 pages.
International Written Opinion for International Application No. PCT/US2019/025177, dated Sep. 3, 2019, 5 pages.
Jouybar et al. "Enhanced Skin Regeneration by Herbal Extract-Coated Poly-L-Lactic Acid Nanofibrous Scaffold" Artif Organs. Nov. 2017; 41(11):E296-E307. doi: 10.1111/aor.12926 (Abstract Only).
Jung et al. "Prospective 1-Year Follow-Up Study of Breast Augmentation by Cell-Assisted Lipotransfer" Aesthetic Surgery Journal 2016, vol. 36(2) 179-190 © 2015 The American Society for Aesthetic Plastic Surgery, Inc.
Kondo et al. "Types of tooth movement, bodily or tipping, do not affect the displacement of the tooth's center of resistance but do affect the alveolar bone resorption" Angle Orthod Jul. 2017; 87(4):563-569.
Lamoureux et al. "Therapeutic Relevance of Osteoprotegerin Gene Therapy in Osteosarcoma: Blockade of the Vicious Cycle between Tumor Cell Proliferation and Bone Resorption" Cancer Res 1 2007 67(15):7308-7318; DOI: 10.1158/0008-5472.CAN-06-4130.
Landau et al. "Review: Proposed Methods to Improve the Survival of Adipose Tissue in Autologous Fat Grafting" Plast Reconstr Surg Glob Open. 2018;6(8):e1870. Published Aug. 3, 2018. doi:10.1097/GOX.0000000000001870.
Liang et al. "Therapeutic effect of low-intensity pulsed ultrasound on temporomandibular joint injury induced by chronic sleep deprivation in rats" Am J Transl Res. 2019; 11(6): 3328-3340.
Martin "Historically significant events in the discovery of RANK/RANKL/OPG" World J Orthop. Oct. 1, 20138; 4(4): 186-197. doi: 10.5312/wjo.v4.i4.186.
McGrath "OPG/RANKL/RANK Pathway as a Therapeutic Target in Cancer" Journal of Thoracic Oncology, Sep. 2011 6(9): 1468-1473.
Norton et al. "Bioelectric Perturbations of Bone: Research Directions and Clinical Applications" Angle Orthod (1984) 54 (1): 73-87.
Novack "Inflammatory osteoclasts, a different breed of bone eaters?" Arthritis Rheumatol. Dec. 2016; 68(12): 2834-2836. doi: 10.1002/art.39835.
Oranger et al. "Cellular Mechanisms of Multiple Myeloma Bone Disease" Clinical and Developmental Immunology vol. 2013, Article ID 289458, 11 pages http://dx.doi.org/10.1155/2013/289458.
Oyajobi "Multiple myeloma/hypercalcemia" Arthritis Research & Therapy vol. 9, Article No. S4 (2007).
Rachner et al. "Prognostic Value of RANKL/OPG Serum Levels and Disseminated Tumor Cells in Nonmetastatic Breast Cancer" Clin Cancer Res Feb. 15, 2019 (25) (4) 1369-1378; DOI: 10.1158/1078-0432.CCR-18-2482.
Raje et al. "Role of the RANK/RANKL Pathway in Multiple Myeloma" Clin Cancer Res 2019 25(1):12-20; DOI: 10.1158/1078-0432.CCR-18-1537.
Showkatbakhsh et al. "Effect of Intra-Canal Direct Current Electric Stimulation on Orthodontic Tooth Movement: An Experimental Study in Canines" Journal of Dental School 2016; 34(3): 157-67.

(56) References Cited

OTHER PUBLICATIONS

Showkatbakhsh et al. "The effect of pulsed electromagnetic fields on the acceleration of tooth movement." World J Orthod. 2010 Winter;11(4):e52-6.
Sisay et al. "The RANK/RANKL/OPG system in tumorigenesis and metastasis of cancer stem cell: potential targets for anticancer therapy" Onco Targets Ther. 2017; 10: 3801-3810.
Sutherland et al. "Prolonged electrical stimulation of the nipples evokes intermittent milk ejection in the anaesthetised lactating rat," Exp Brain Res. 1987;66(1):29-34.
Tan et al. "Bioelectric Perturbations in Orthodontic tooth movement" 2010 Journal of Dental Sciences & Research 1:1: pp. 41-49.
Tokyo Medical and Dental University "RANKL expressed by osteocytes has an important role in orthodontic tooth movement" Science Daily Oct. 20, 2017.
Van Dam et al. "RANK/RANKL signaling inhibition may improve the effectiveness of checkpoint blockade in cancer treatment" Critical Reviews in Oncology/Hematology vol. 133, Jan. 2019, pp. 85-91.
Verna et al. "The rate and the type of orthodontic tooth movement is influenced by bone turnover in a rat model" European Journal of Orthodontics 22 (2000) 343-352.
Wang et al. "Local and sustained miRNA delivery from an injectable hydrogel promotes cardiomyocyte proliferation and functional regeneration after ischemic injury", Nat Biomed Eng. 2017; 1: 983-992, doi: 10.1038/s41551-017-0157-y.
Yang "Effect RANKL Produced by Periodontal Ligament Cells on Orthodontic Tooth Movement" (2016) Dental Theses. Paper 13.
Zaniboni et al. "Do electrical current and laser therapies improve bone remodeling during an orthodontic treatment with corticotomy?" Clin Oral Invest 23, 4083-4097 (2019). https://doi.org/10.1007/s00784-019-02845-9.

\* cited by examiner

BIOELECTRIC BLOOD PRESSURE MANAGEMENT

CROSS-REFERENCE TO RELATED APPLICATIONS

This application is a continuation-in-part of U.S. patent application Ser. No. 15/812,760, filed on Nov. 14, 2017 and a continuation-in-part of U.S. patent application Ser. No. 15/460,129, filed on Mar. 15, 2017 (U.S. 2017/0266371A1, Sep. 21, 2017), now U.S. Pat. No. 10,646,644 B2 (May 12, 2020), which itself claims the benefit under 35 USC § 119 of:

U.S. Provisional Patent Application Ser. No. 62/308,702, filed Mar. 15, 2016;
U.S. Provisional Patent Application Ser. No. 62/363,012, filed Jul. 15, 2016;
U.S. Provisional Patent Application Ser. No. 62/364,472, filed Jul. 20, 2016;
U.S. Provisional Patent Application Ser. No. 62/375,271, filed Aug. 15, 2016;
U.S. Provisional Patent Application Ser. No. 62/385,124, filed Sept. 8, 2016;
U.S. Provisional Patent Application Ser. No. 62/454,521, filed Feb. 3, 2017; and
U.S. Provisional Patent Application Ser. No. 62/352,930, filed Jun. 21, 2016, the disclosure of each of which is incorporated herein in its entirety by this reference.

FIELD

The application relates generally to the field of medical devices and associated treatments, and more specifically to precise bioelectrical stimulation of a subject's tissue useful to control, manage, and/or modulate the subject's blood pressure.

BACKGROUND

Blood pressure is simply the physical pressure of blood in the blood vessels. It is similar to the concept of air pressure in a car tire. A common blood pressure might be 120/80 (stated as "120 over 80"). These values are quoted in units known as millimeters of mercury (mmHg). There are two numbers because the blood pressure varies with the heartbeat. The higher pressure (e.g., 120) represents the pressure in the arteries when the heart beats, pumping blood into the arteries. This pressure is called systolic pressure. The lower pressure (80) represents the pressure in the arteries when the heart is relaxed between beats. This pressure is called "diastolic pressure."

Blood pressures differ between individuals. Some people have low, some average and some high blood pressure levels.

There are various definitions of high blood pressure, which is also known as hypertension, but most doctors consider blood pressures of 140/90 and greater to be high. The precise values that doctors might interpret as high blood pressure depend to an extent on individual circumstances. For example, in patients with diabetes, the definition of hypertension is considered by some to be pressures greater than 130/80.

Left unchecked, high blood pressure will over the years cause damage to the blood vessels of the subject's heart and brain that leads to heart attacks and strokes. It also places extra strain on the heart, causing thickening of the heart muscle and heart failure and it damages the kidneys and can lead to kidney failure.

Hypertension is a large burden to patient health and health care costs. Despite various options, more 30% of patients do not respond sufficiently to medical treatment. Mechanoreceptors in the aortic arch relay blood pressure (BP) levels through vagal nerve (VN) fibers to the brainstem and trigger the baroreflex, lowering the BP. Selective electrical stimulation of these nerve fibers reduced BP in rats.

More than 1 billion people suffer from high blood pressure worldwide. Blood pressure levels have been shown to be positively and continuously related to the risk for stroke and coronary heart disease. In some age groups, the risk of cardiovascular disease doubles for each increment of 20/10 mmHg of blood pressure, starting as low as 115/75 mmHg. In addition to coronary heart diseases and stroke, complications of raised blood pressure include heart failure, peripheral vascular disease, renal impairment, retinal hemorrhage and visual impairment. Treating systolic blood pressure and diastolic blood pressure until they are less than 140/90 mmHg is associated with a reduction in cardiovascular complications.

BRIEF SUMMARY

Described are a system and method that utilize bioelectric signaling to balance electrical potentials in a subject's body via neuro-hormonal circuit loops, to increase elasticity of the subject's arteries to promote protein release to dampen arterial blood pressure, and to change arterial electrical charges to reduce narrowing of the arteries.

The described system is designed to localize and stimulate the fibers inside the VN without inadvertent stimulation of non-baroreceptive fibers causing side effects like bradycardia and bradypnea. The system also controls release of specific proteins known to lower blood pressures including tropoelastin (known to increase elasticity in the aorta and other peripheral blood vessels).

Bioelectric stimulation as described herein is thought to address two known root causes of hypertension. First, loss of arterial compliance and, second, in-balance of electrical potentials within the body. The system and method are designed to reduce loss of arterial compliance by controlled release of a number of growth factors that promote increased elasticity in the arteries including tropoelastin, SDF-1, VEGF, IGF-1, PDGF and HGF.

A theory exists that during a hypertension prophase episode, there may appear abnormal movement for cell membrane ions, the pathological electric potentials. This electrical abnormality of blood vessel signal controls may then be followed by the phenomena of slowed blood flow, small artery spasms, and increased blood vessel compliance resistance, finally leading to the rise of blood pressure.

The bioelectric signals sequence for lowering blood pressure is designed to be applied to the subject's body with its transmitted bioelectric signals intended to activate the bioelectric circuits in the body, changing abnormal current flow patterns back to normal. It is designed to directly adjust the pathological electrical ionic membrane potentials, arterial muscle cells, and relieve small artery spasm. The intent is also to strengthen red blood cell surface repulsion to reduce blood magnetic viscosity, and thus lower vessel and blood stream flow resistance. The described system and method are designed to additionally then lead to continued regulation and integration in attempting to clear and dissolve cholesterol and neutral fat deposited on the tunica intima of arteries to remove stasis in the blood vessels. Thus, system and methods are not only designed for acute decreases in blood pressure, but also to maintain a continuous effect for long term action in attempting to address the root causes of hypertension and thus many secondary to hypertension related cardiovascular diseases.

The described system and method are designed to address high blood pressure in a subject via three primary means.

First, bioelectric signaling to the brain's blood pressure control center and send closed feedback loop real time. The stimulators of the system may be placed in any innervated area such as the forearm. Placed just under the skin, they are designed to activate bioelectrical signaling via the nervous system. The system's stimulator(s) sense and send bioelectrical signals to modulate the subject's blood pressure. The system emits very low-power, natural level, bioelectric stimulation sequences that communicate with the subject's brain. These bioelectric signals travel to the hypothalamus midbrain, and the medulla; the signal has multiple pathways to the brain's blood pressure control center. This bioelectric signaling in a closed feedback loop is designed to modulate and normalize blood pressure. The system is the only one known at this time that senses real time the needs of the subject, and then adjusts the bioelectric signaling to meet the individual's needs for blood pressure control on a real time basis.

Second, bioelectric signaling is delivered to improve the elasticity of arteries, especially the aorta, to improve blood pressure dampening. The bioelectric stimulator controls protein expressions, such as tropoelastin, SDF1, IGF1, EGF, CXCL5, and follistatin, which improve elasticity of arteries.

Third, bioelectric signaling is applied to the subject to prevent artery flow narrowing and spasms. The bioelectric stimulator directs the release of proteins and bioelectric signals designed to inhibit plaque and blood clot formations and artery spasms which increase blood pressure and heighten the risk of a heart attack, stroke or limb amputation. The bioelectric signals for proteins such as PDGF, SDF1, VEGF, HIF1α, CXCL5, EGF, HGF and eNOS also are designed to grow new blood vessels with mature healthy endothelium linings and dilate existing blood vessels, via eNOS expression, which also can serve to lower high blood pressure.

In certain embodiments, described is a system with control with selective vagal nerve stimulation.

The system and method are designed to be delivered via skin surface or low depth implantable ultra-low power signal sensors and signal generating processors.

The system and method are designed to control release of proteins that improve elasticity of the aorta and other peripheral vessels so that the blood pressure has a dampening relief system within the body as is found in normal healthy subjects.

In certain embodiments, the system and method utilize low depth, implantable ultra-low power signal sensors.

The system seeks to develop a method for selective vagus nerve stimulation to reduce high blood pressure (hypertension) without triggering bradycardia or bradypnea.

In certain embodiments, baroreceptor compound activity is localized using multiple non-invasive bioelectric sensors with information sent to a microprocessor that then delivers a customized bioelectric signaling sequence via quad polar stimulation near the barofibers. Constant feedback loops adjust and vary the stimulation pulse, width, and duration.

In certain embodiments, the system is designed to lower high blood pressure by improving elastic compliance of the aorta and other arteries and bioelectric potentials balance management throughout the body.

Certain embodiments of devices for use with the system and methods described herein preferably have the following features. Such a device has three primary components of blood pressure control therapy. First, wireless bioelectric signals for increasing arterial compliance via controlled release of growth factors such as tropoelastin. Second, wireless bioelectric signals to manage the control of blood pressure between the brain and hormonal glands. Third, bioelectric signals delivered via the nervous and cardiovascular system to manage total body electrical potentials balance.

Described is a bioelectric stimulator including: a power source (e.g., battery, capacitor, or other suitable source of electricity), and means for delivering an electrical signal to a subject's tissue (e.g., via electrode(s) or wirelessly). The bioelectric stimulator utilizes the electrical signal to precisely control protein expression in the tissue on demand. Such a bioelectric stimulator preferably precisely controls release of SDF-1 in the subject, without diminishing effect over time.

Also described is a method of using the bioelectric stimulator to control a subject's blood pressure, the method including: delivering selected electrical signals to the organ so as to precisely control protein expressions in the right sequence and volume for total or near total blood pressure control.

A preferred system includes: a bioelectric stimulator that controls/stimulates the release/production of SDF1, IGF1, EGF, HGF, PDGF, eNOS, VEGF, follistatin, HIF1α, and/or tropoelastin in a subject.

DETAILED DESCRIPTION

Figure 1:
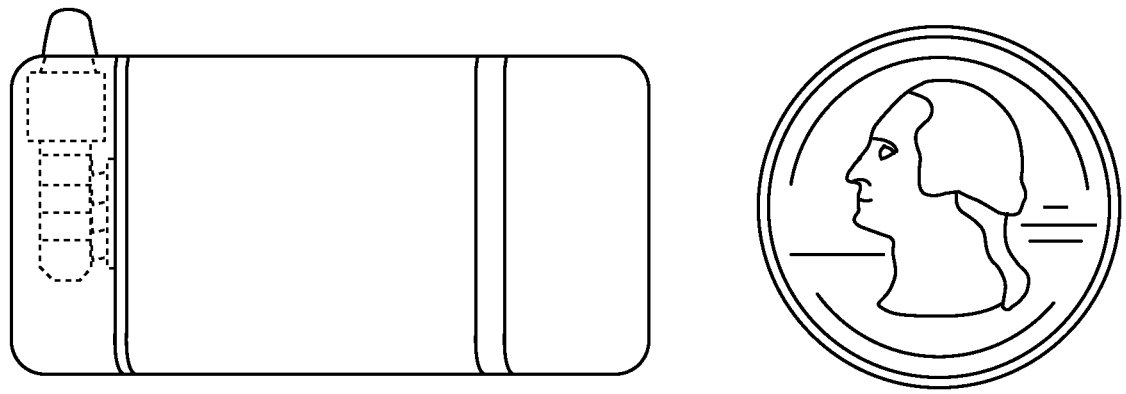
FIG. 1 depicts a programmed bioelectric stimulator depicted alongside a U.S. quarter.

Referring now to FIG. 1, depicted is a human use stimulator for use herein. Preferably, such a device is about the size of two quarters (available from QIG Greatbatch/Greatbatch, Inc. of Frisco, Tex., US) and is programmable.

Figure 2:
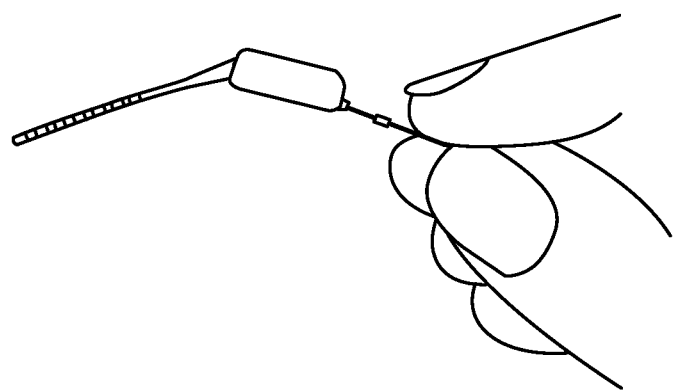
FIG. 2 depicts a device according to the description.

A preferred device (FIG. 2) is about the size of a U.S. quarter dollar piece.

When arteries get stiff and hardened, the body loses its main natural blood pressure dampening system and high blood pressure sets in. Secondarily the bioelectric current potentials management between the brain, the hormonal glans of the body and arterial walls must be in balance for healthy blood pressure. The described device is designed to address multiple known root causes of hypertension.

There exists a close relationship between bioelectricity and hypertension. Bioelectric stimulation may address two known root causes of hypertension, i.e., the loss of arterial compliance and in-balance of electrical potentials within the body.

The described system and method are designed to reduce loss of arterial compliance by controlled release of a number of growth factors that promote increased elasticity in the arteries including tropoelastin, SDF-1, VEGF, IGF-1, PDGF and HGF.

While not intending to be bound by theory, the following might help explain the invention. A number of scientists propose the theory that during the hypertension prophase episode, there may appear abnormal movement for cell membrane ions, the pathological electric potentials. This electrical abnormality of blood vessel signal controls may then be followed by the phenomena of slowed blood flow, small artery spasms, and increased blood vessel compliance resistance, finally leading to the rise of blood pressure.

The bioelectric signals sequence described herein for lowering blood pressure is designed to be applied to the body with its transmitted bioelectric signals intended to activate the bioelectric circuits in the body changing abnormal current flow patterns back to normal. It is designed to directly adjust the pathological electrical ionic membrane potentials, arterial muscle cells, and relieve the small artery spasm. The intent is also to strengthen red blood cell surface repulsion to reduce blood magnetic viscosity, and thus lower vessel and blood stream flow resistance. The described system and method are designed to additionally then lead continued regulation and integration in attempting to clear and dissolve cholesterol and neutral fat deposited on the tunica intima of arteries to remove stasis in the blood vessels. Thus, the described system and method are not only designed for acute decreases in blood pressure, but also to maintain a continuous effect for long term action in attempting to address the root causes of hypertension and thus many secondary to hypertension related cardiovascular diseases.

In certain embodiments, the disclosure includes a method of controlling blood pressure in a subject, the method comprising: delivering selected bioelectric signals to the subject's tissue so as to enhance the release and/or expression of proteins that reduce the subject's blood pressure. In such a meth, the proteins preferably comprise proteins selected from the group consisting of stromal cell-derived factor 1 ("SDF1"), vascular endothelial growth factor ("VEGF"), insulin-like growth factor 1 ("IGF1"), platelet-derived growth factor ("PDGF"), tropoelastin, hepatocyte growth factor ("HGF"), and any combination thereof. The proteins may further include protein(s) selected from the group consisting of IGF1, epidermal growth factor ("EGF"), CXCL5, hypoxia-inducible factor 1-alpha ("HIF1a"), endothelial NOS ("eNOS"), follistatin, and a combination of any thereof. In certain embodiments, the subject's tissue to be treated preferably comprises fiber inside the vagus nerve. Preferably, the subject's tissue does not comprise non-baroreceptor fibers.

Generally, the system hereof involves a bioelectric stimulator controlling release of SDF-1, IGF-1, HGF, EGF, VEGF, PDGF, eNOS, follistatin, and tropoelastin. Optionally, other proteins and/or hormones may be included.

SDF-1 is generally for recruiting stem cells and maturing blood vessels. IGF-1 is for DNA repair. HGF is for tissue regeneration and reduces arrhythmias in the case of heart. EGF grows tissue. VEGF grows blood vessels. PDGF is a second stem cell homing factor and helps tissue regeneration especially heart. eNOS dilates blood vessels. Follistatin promotes muscle growth. Tropoelastin increases elasticity of all tissues especially arteries, skin, heart, aorta.

The micro voltage signal generator may be produced utilizing the same techniques to produce a standard heart pacemaker well known to a person of ordinary skill in the art. An exemplary microvoltage generator is available (for experimental purposes from Cal-X Stars Business Accelerator, Inc. DBA Leonhardt's Launchpads or Leonhardt Vineyards LLC DBA Leonhardt Ventures of Salt Lake City, Utah, US). The primary difference is the special electrical stimulation signals needed to control, e.g., precise follistatin release on demand (which signals are described later herein). The leading pacemaker manufacturers are Medtronic, Boston Scientific Guidant, Abbott St. Jude, BioTronik and Sorin Biomedica.

Construction of the electric signal generators and pacemakers, are known in the art and can be obtained from OEM suppliers as well as their accompanying chargers and programmers. The electric signal generators are programmed to produce specific signals to lead to specific protein expressions at precisely the right time for, e.g., optimal organ treatment or regeneration.

The pacing infusion lead may be constructed or purchased from the same suppliers that build standard heart pacemaker leads. Pacing infusion leads may be purchased from a variety of OEM vendors. The pacing infusion lead may, for example, be a standard one currently used in heart failure pacing studies in combination with drug delivery.

An infusion and electrode wide area pitch may be constructed by cutting conduction polymer to shape and forming plastic into a flat bag with outlet ports in strategic locations.

Micro stimulators may be purchased or constructed in the same manner heart pacemakers have been made since the 1960's. The programming computer can be standard laptop computer. The programming wand customary to wireless programming wands may be used to program heart pacers.

Wireless, single lumen infusion pacing lead or infusion conduction wide array patch may all be used to deliver the regeneration signals and substances to the organ of interest to be treated or they may be used in combination.

A re-charging wand for use herein is preferably similar to the pacemaker re-charging wand developed by Alfred Mann in the early 1970's for recharging externally implantable pacemakers.

Bioelectric stimulation can be done with a microstimulator having a pacing infusion lead with a corkscrew lead placed/attached at, e.g., the center of heart scar tissue. The microstimulator is actuated and runs through programmed signals to signal the release of, e.g., SDF-1. Described is a method of activating a tissue to differentiate a stem cell or to stimulate the tissue to produce a protein. The protein is selected from the group consisting of insulin-like growth factor 1 ("IGF1"), epidermal growth factor ("EGF"), hepatocyte growth factor ("HGF"), platelet-derived growth factor ("PDGF"), endothelial NOS ("eNOS"), vascular endothelial growth factor ("VEGF"), tumor necrosis factor alpha ("TNF A"), follistatin, hypoxia-inducible factor 1-alpha ("HIF1α"), and tropoelastin, the method including: stimulating the, e.g., human tissue with an electrical signal appropriate for the protein and tissue.

In such a method, when the electrical signal includes (within 15%): 0.1 V applied at a frequency of about 50 Hz with a duration of about three (3) minutes (wherein the electrical signal is as measured three (3) mm deep into the tissue), the protein produced is VEGF.

In such a method, when the electrical signal includes (within 2%): 200 picoamps for about 10 seconds for about one (1) hour and the pulse has an amplitude of about 5 volts and a width of about 0.5 milliseconds for about 1 hour, with a duration of about one (1) minute (wherein the electrical signal is as measured three (3) mm deep into the tissue), stem cells differentiate.

In such a method, when the electrical signal includes (within 15%): 10 V at 50 Hz and 100 Hz for about 12 hours each (duration 1 minute) (wherein the electrical signal is as measured three (3) mm deep into the tissue), the protein produced is follistatin.

In such a method, when the electrical signal includes (within 15%): 3.5 V stimulation in 10 second bursts, 1 burst every 30 seconds at a frequency of about 50 Hz (duration 5 minutes) (wherein the electrical signal is as measured three (3) mm deep into the tissue), the protein produced is HGF.

In such a method, when the electrical signal includes (within 15%): 3 mV with a frequency of about 22 Hz, and a current of about 1 mA for about fifteen (15) minutes and 3 mA for about fifteen (15) minutes (duration 5 minutes) (wherein the electrical signal is as measured three (3) mm deep into the tissue), the protein produced is IGF-1.

In such a method, when the electrical signal includes (within 15%): 0.06 V with 50 Hz alternating electrical field and a current of about 1 mA for about fifteen (15) minutes and 3 mA for about fifteen (15) minutes (duration 2 minutes) (wherein the electrical signal is as measured three (3) mm deep into the tissue), the protein produced is tropoelastin.

In such a method, when the electrical signal includes (within 15%): alternating high-frequency (HF) and medium-frequency signals (MF), symmetric, biphasic, trapezoid pulses, with 400-μs pulse duration and 1.5/1-s ramp-up/ramp-down duration, respectively (wherein the electrical signal is as measured three (3) mm deep into the tissue), the protein produced is eNOS. In such a method, when the HF consists of about 75 Hz pulses with six (6) seconds on and 21 seconds off for about fifteen (15) minutes. In such a method, when the MF consists of about 45 Hz pulses with 5 seconds on 12 seconds off for about fifteen (15) minutes followed by stimulation duration set as 20 minutes. In such a method, when the electrical signal includes (within 15%): 1 Hz stimulation, stimulation applied for about nine (9) seconds, followed by a one (1) second silent period, a total of about 1080 stimulations for about 20 minutes. In such a method, when the electrical signal includes (within 15%): 20 Hz stimulation, stimulation applied for about two (2) seconds, followed by silent period for about 28 seconds, a total of about 1600 stimulations for about 20 minutes (duration 2 minutes).

In such a method, when the electrical signal includes (within 15%): 10 V/cm, pulse-width 180 μs, 500 Hz (duration nine (9) minutes) (wherein the electrical signal is as measured three (3) mm deep into the tissue), the protein produced is EGF.

For example, upregulation of IGF-1, VEGF, and SDF-1 was achieved in cardiomyocytes using such signals. Upregulation of SDF-1 was achieved in pig heart. Upregulation of VEGF, endothelial NOS ("eNOS"), and HIF1α was achieved in eye cells.

Also described is a method of activating a tissue to produce stromal cell-derived factor 1 ("SDF1"), the method including: stimulating the (e.g., human) tissue with an electrical signal, wherein the electrical signal includes (within 15%): 30 pulses per second with a voltage of about 3.5 mV, and successively alternating currents of about 700 to 1500 picoamps for about one minute, and again with 700 to 1500 picoamps for about one minute and stimulated with current of about 0.25 mA, pulse duration of about 40 pulses/s, pulse width of about 100 μs, wherein the electrical signal is as measured three (3) mm deep into the tissue.

Further described is a method of activating a tissue to attract a stem cell, the method including: stimulating the (e.g., human) tissue with an electrical signal, wherein the electrical signal includes (within 2%): fifteen (15) mV and a current of about 500 picoamps at 70 pulses per minute for about three (3) hours and 20 pulses per minute, a pulse amplitude of from about 2.5-6 volts, and a pulse width of from about 0.2-0.7 milliseconds for about three (3) hours for about three (3) minutes, wherein the electrical signal is as measured three (3) mm deep into the tissue.

In some cases, SDF-1 recruits via a presumed homing signal new reparative stem cells to the damaged organ. VEGF causes new nutrient and oxygen producing blood vessels to grow into the area being treated. IGF-1 repairs damaged cells, tissues and organs. Follistatin repairs damaged muscle. Tropoelastin adds elasticity to treated tissues making them more compliant. HGF aides in all repair processes and in the specific case of the heart regeneration reduces the risk of arrhythmias. All of these proteins work together to fully regenerate an organ over time.

What follows are preferred signals from the stimulator. For example, described are two PDGF expression control signals, one low voltage and one higher voltage. The test tissue is sheep heart tissue. The test cells are mesenchymal stem cells.

30% PDGF increase>3 V/cm, 10 Hz, 2 micro amps (0.000002 amps) and the pulse duration 0.2 ms.

230% PDGF increase>20 V/cm 100 Hz, 0.25 mA (2.5e-7 amps) and pulse duration of 40 pulses/s, width of 100 μs.

40-minute treatment cycles 2 times a week for 4 weeks and then 3 times a week for 12 weeks.

PDGF Signal: 20 V for 1 minute, 20 MVs for 10 minutes, current of 0.25 mA, pulse duration of 40 pulses/s, pulse width of 100 μs, and frequency of 100 Hz for 5 minutes followed by 528 Hz for 3 minutes and 432 Hz for 3 minutes and 50 Hz for 3 minutes.

VEGF—Blood vessel sprouting growth: 0.1 V applied at a frequency of 50 Hz. Duration 3 minutes.

SDF-1—Stem cell recruiting signal: 30 pulses per second with a voltage of 3.5 mV, and successively alternating currents of 700 to 1500 picoamps for one minute, and again with 700 to 1500 picoamps for one minute and stimulated with current of 0.25 mA, pulse duration of 40 pulses/s, pulse width of 100 µs, and frequency of 100 Hz—each signal for 40 minutes to 8 hours a day for 2 to 36 months as needed for ideal results. Duration 7 minutes.

Stem cell differentiation signals to become muscle: 200 picoamps for 10 seconds for 1 hour and the pulse has an amplitude of 5 volts and a width of 0.5 milliseconds for 1 hour. Duration 1 minute.

Another method is to reverse polarity and drop the voltage.

Follistatin—(muscle growth) production signal: 10 V at 50 Hz and 100 Hz 0.25 mA. Duration 1 minute.

HGF—Hepatocyte growth factor (arrhythmia reduction) signal: 3.5 V stimulation in 10 second bursts, 1 burst every 30 seconds at frequency 50 Hz. Duration 5 minutes.

IGF-1: 3 mV with electric frequency of 22 Hz, and electric current of 1 mA for 15 minutes and 3 mA for 15 minutes. Duration 5 minutes.

Tropoelastin: 0.06 V with 50 Hz alternating electrical field and electric current of 1 mA for 15 minutes and 3 mA for 15 minutes. Duration 2 minutes.

eNOS: Alternating high-frequency (HF) and medium-frequency signals (MF): Symmetric, biphasic, trapezoid pulses, with 400-µs pulse duration and 1.5/1 -s ramp-up/ramp-down duration, respectively. HF consisted of 75 Hz pulses with 6 seconds on-21 seconds off for 15 minutes. MF consisted of 45 Hz pulses with 5 seconds on-12 seconds off for 15 minutes. Followed by stimulation duration set as 20 minutes for both 1 Hz and 20 Hz stimulations. For 1 Hz stimulation, stimulation is applied for 9 seconds, followed by a 1 second silent period, a total of 1080 stimulations for 20 min. For 20 Hz stimulation, stimulation is applied for 2 seconds, followed by silent period for 28 seconds, a total of 1600 stimulations for 20 min. Duration 2 minutes.

EGF—10 V/cm, pulse-width 180 µs, 500 Hz. Duration 9 minutes.

FIGS. 3-12 are images of the corresponding signals with the name, voltage, and frequency of each signal written on each image. eNOS and differentiation signals were omitted due to of complexity or lack of frequency parameters. The signals are to be further defined in terms of current and frequency, not voltage and frequency as shown. The voltage delivered to the cells will be different for each tissue type, but with current all of the signals can be kept constant regardless of tissue type. The device should have a current driven signal (instead of voltage driven like most other devices).

Figure 3:
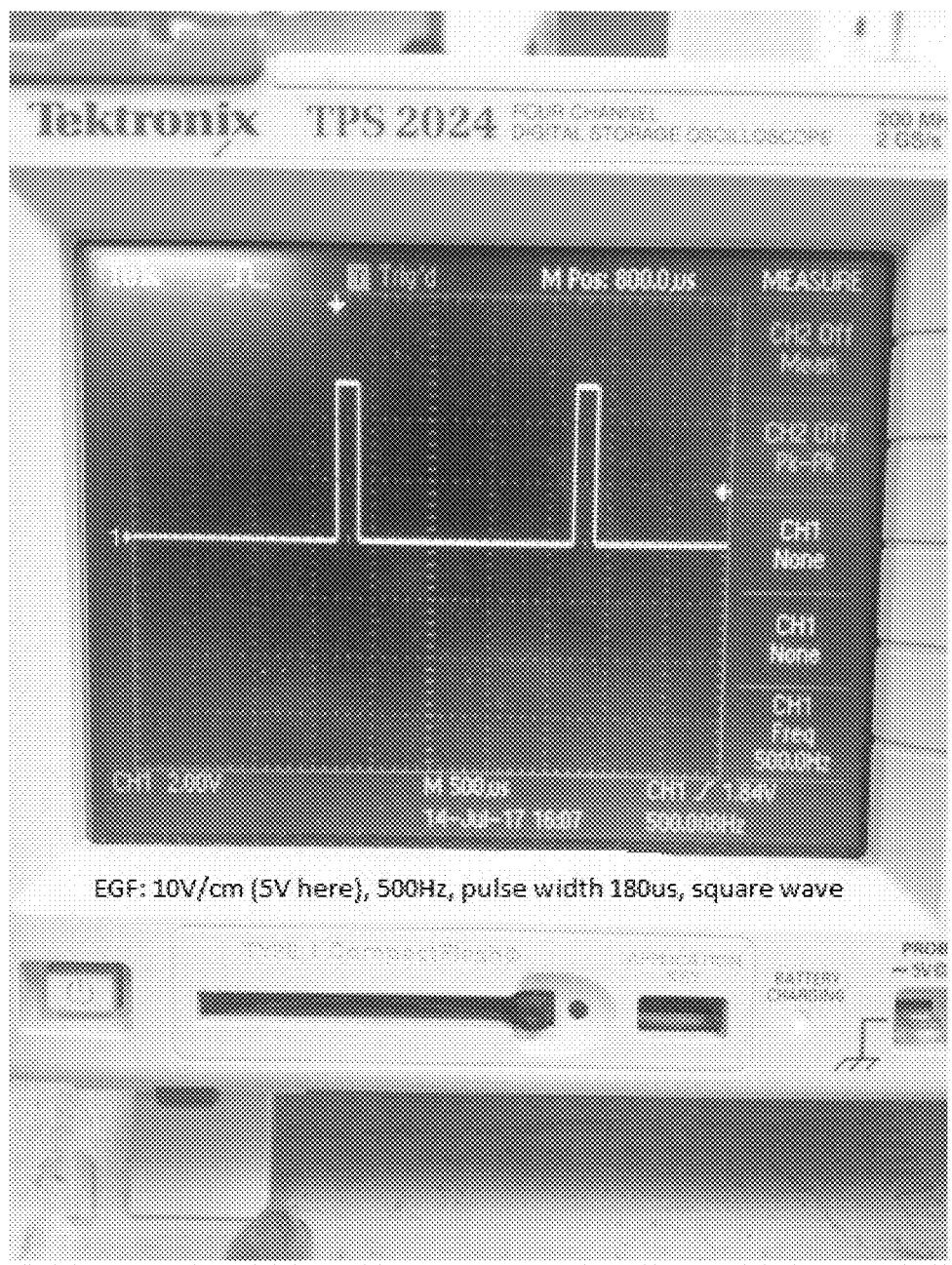
FIG. 3 depicts an image of the signal (voltage and frequency) associated with EGF at 10 V/cm (5 V here), 500 Hz, pulse width 180 µs, square wave.
Figure 4:
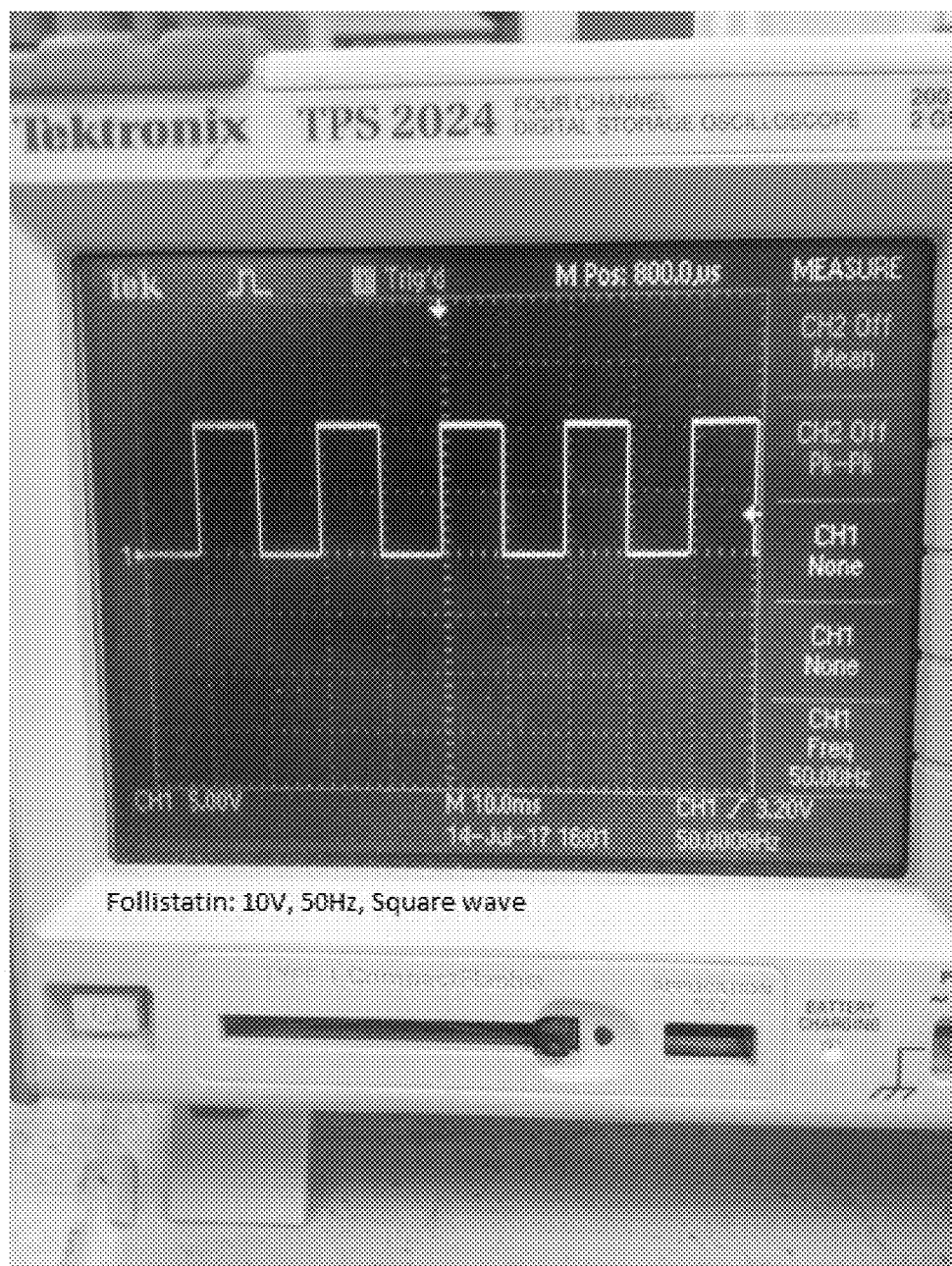
FIG. 4 depicts an image of the signal (voltage and frequency) associated with follistatin at 10 V/cm, 50 Hz, square wave.
Figure 5:
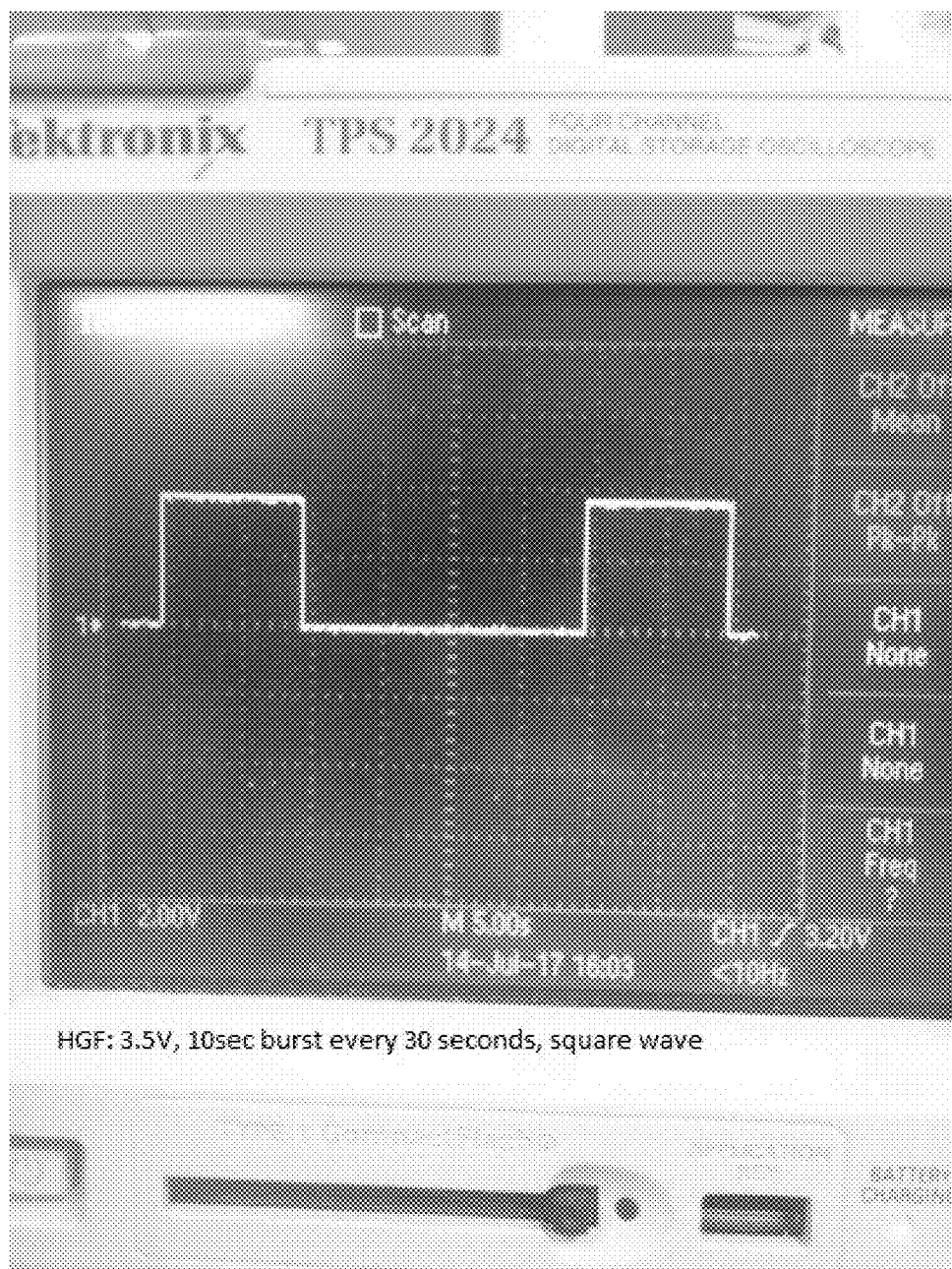
FIG. 5 depicts an image of the signal (voltage and frequency) associated with HGF at 3.5 V, 10 second burst every 30 seconds, square wave.
Figure 6:
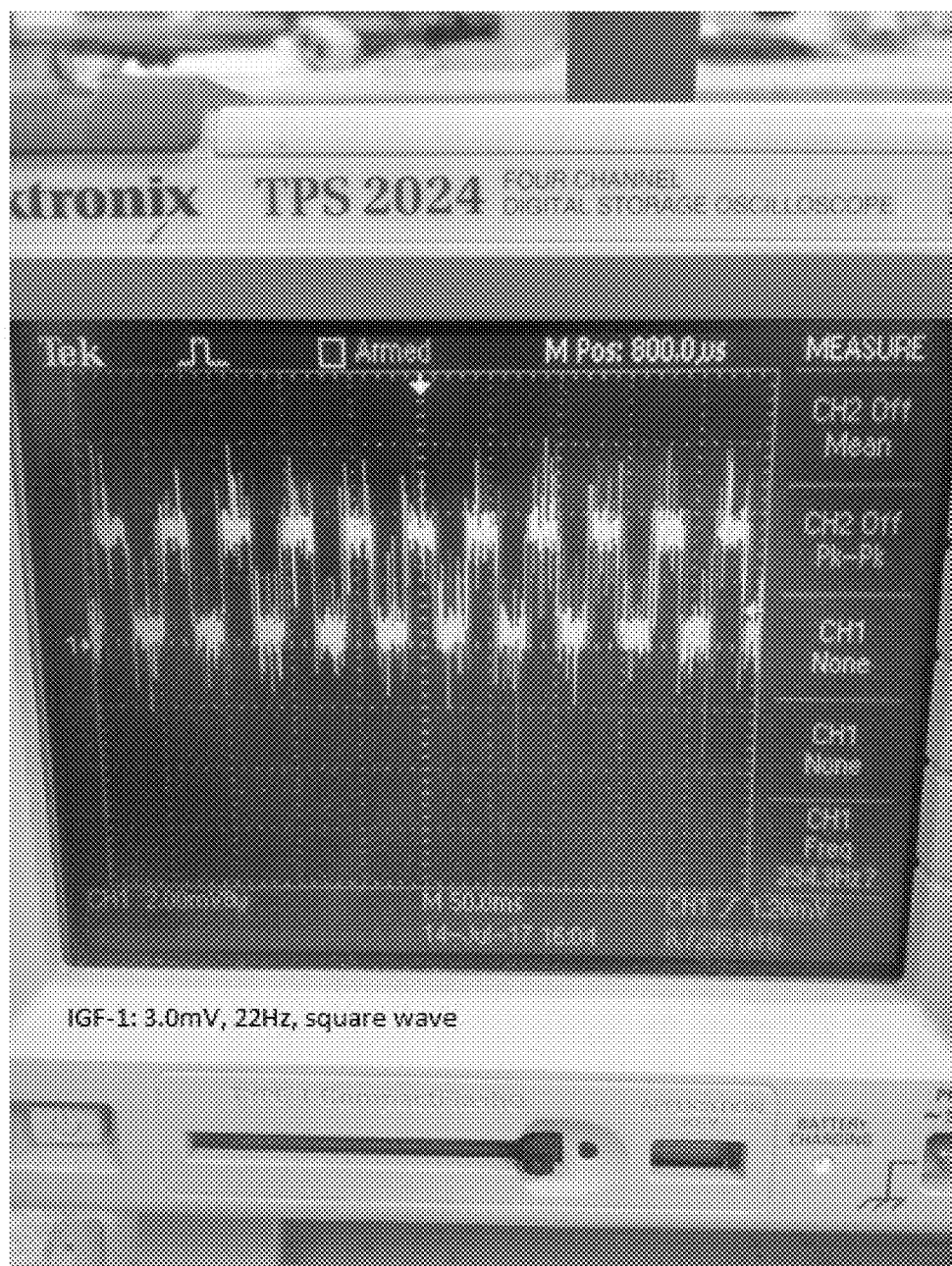
FIG. 6 depicts an image of the signal (voltage and frequency) associated with IGF-1: 3.0 mV, 22 Hz, square wave.
Figure 7:
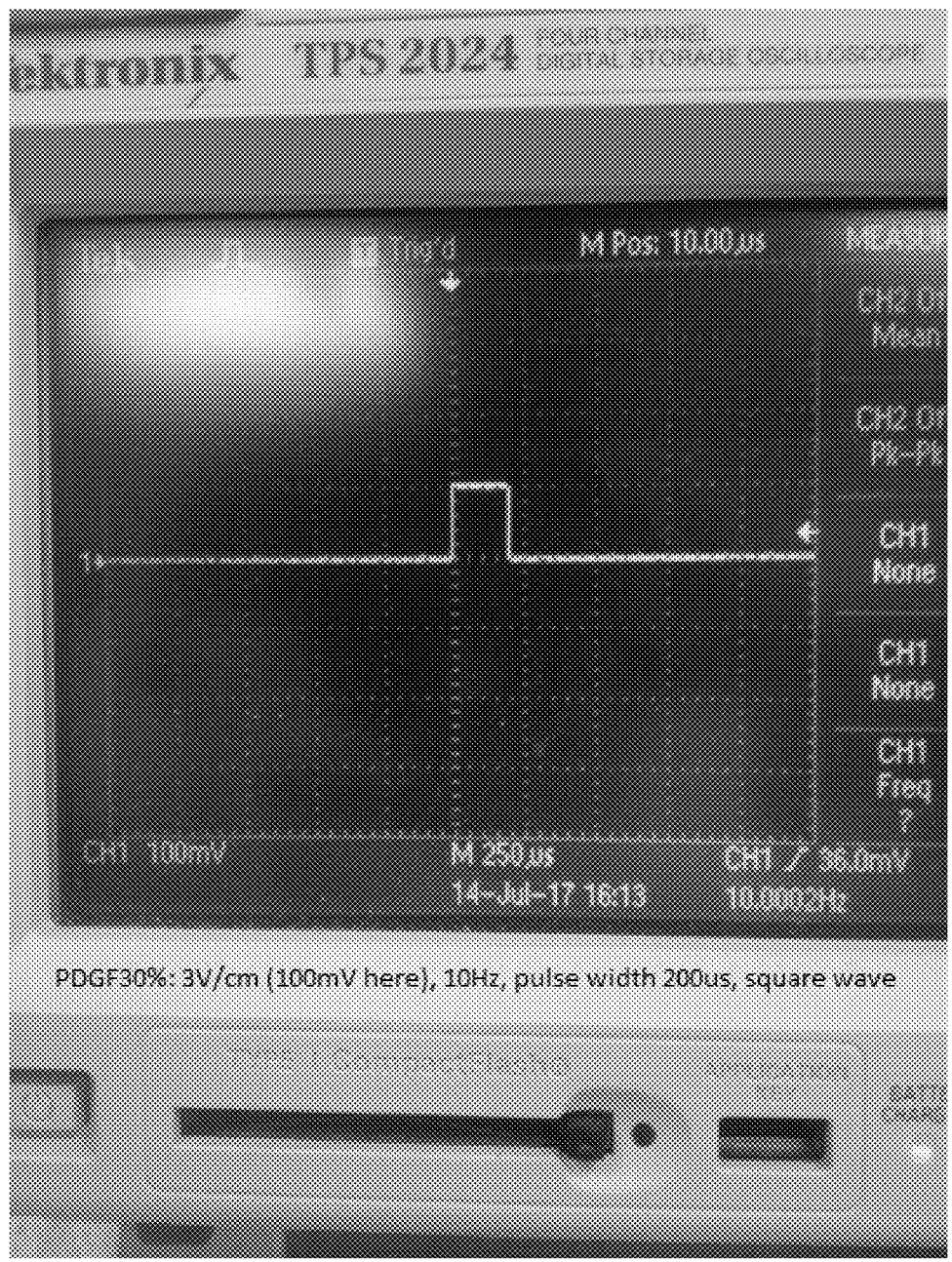
FIG. 7 depicts an image of the signal (voltage and frequency) associated with PDGF 30%: 3 V/cm (100 mV here), 10 Hz, pulse width 200 µs, square wave.
Figure 8:
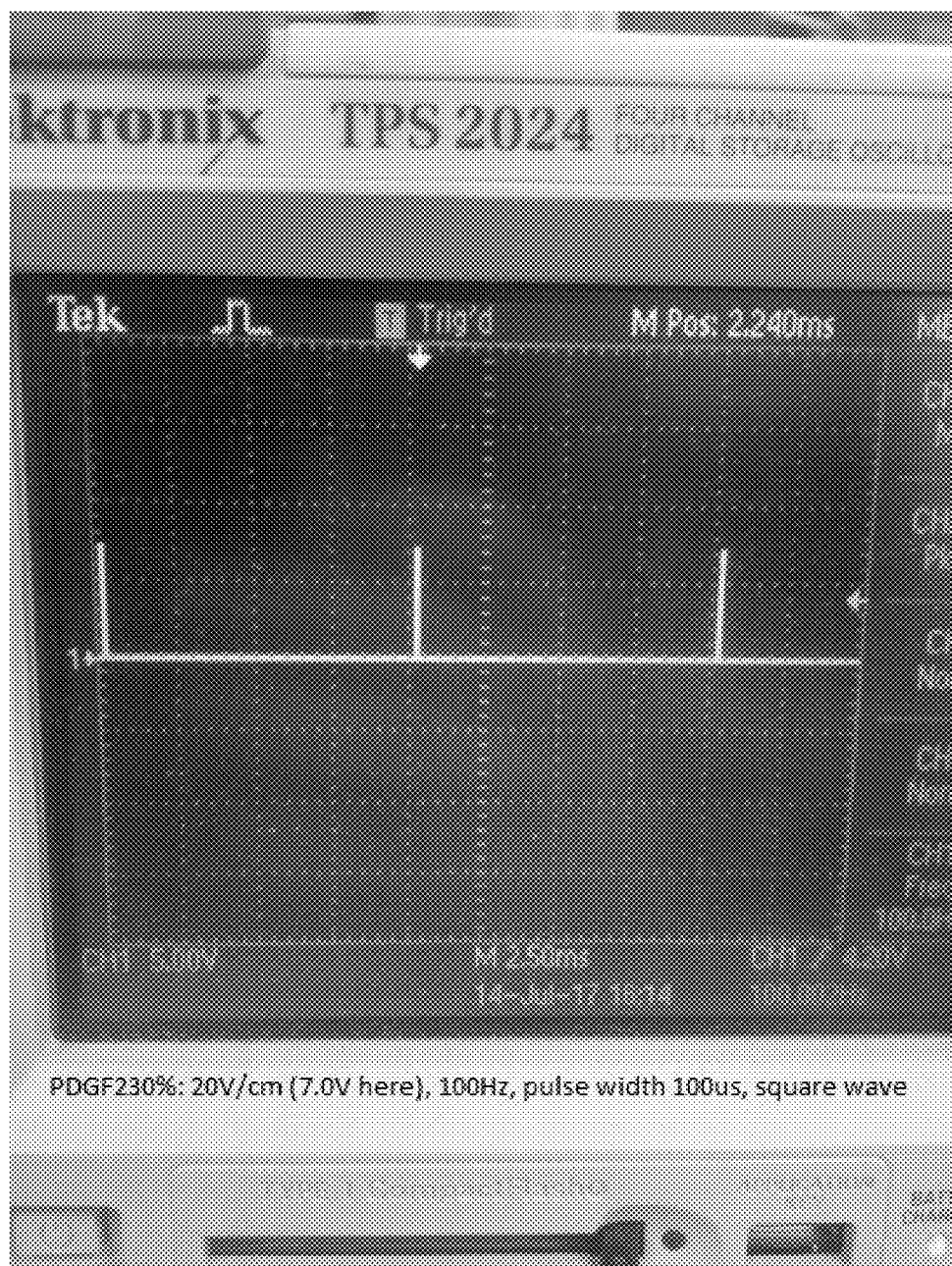
FIG. 8 depicts an image of the signal (voltage and frequency) associated with PDGF 230%: 20 V/cm (7.0 V here), 100 Hz, pulse width 100 µs, square wave.
Figure 9:
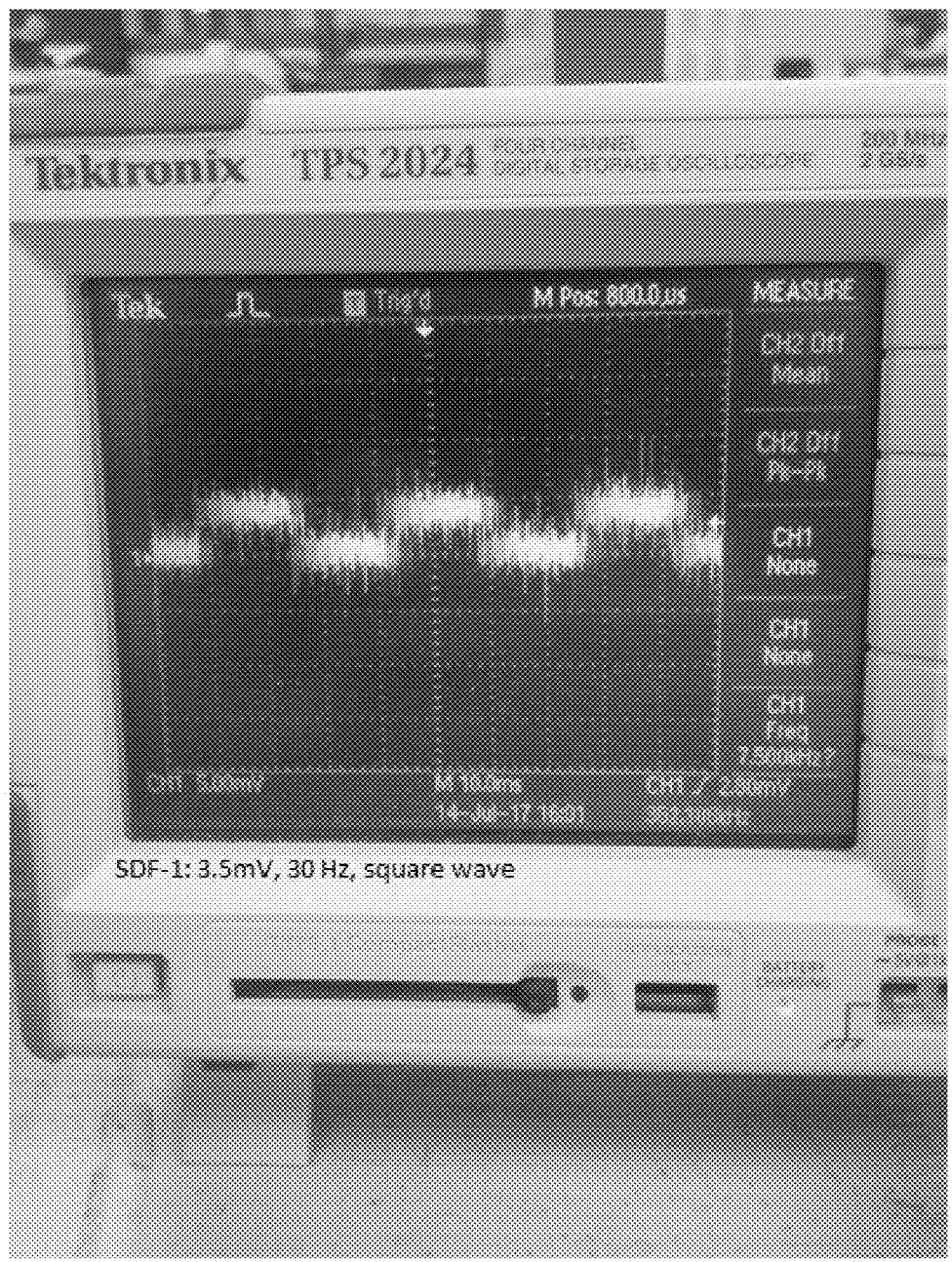
FIG. 9 depicts an image of the signal (voltage and frequency) associated with SDF-1: 3.5 mV, 30 Hz, square wave.
Figure 10:
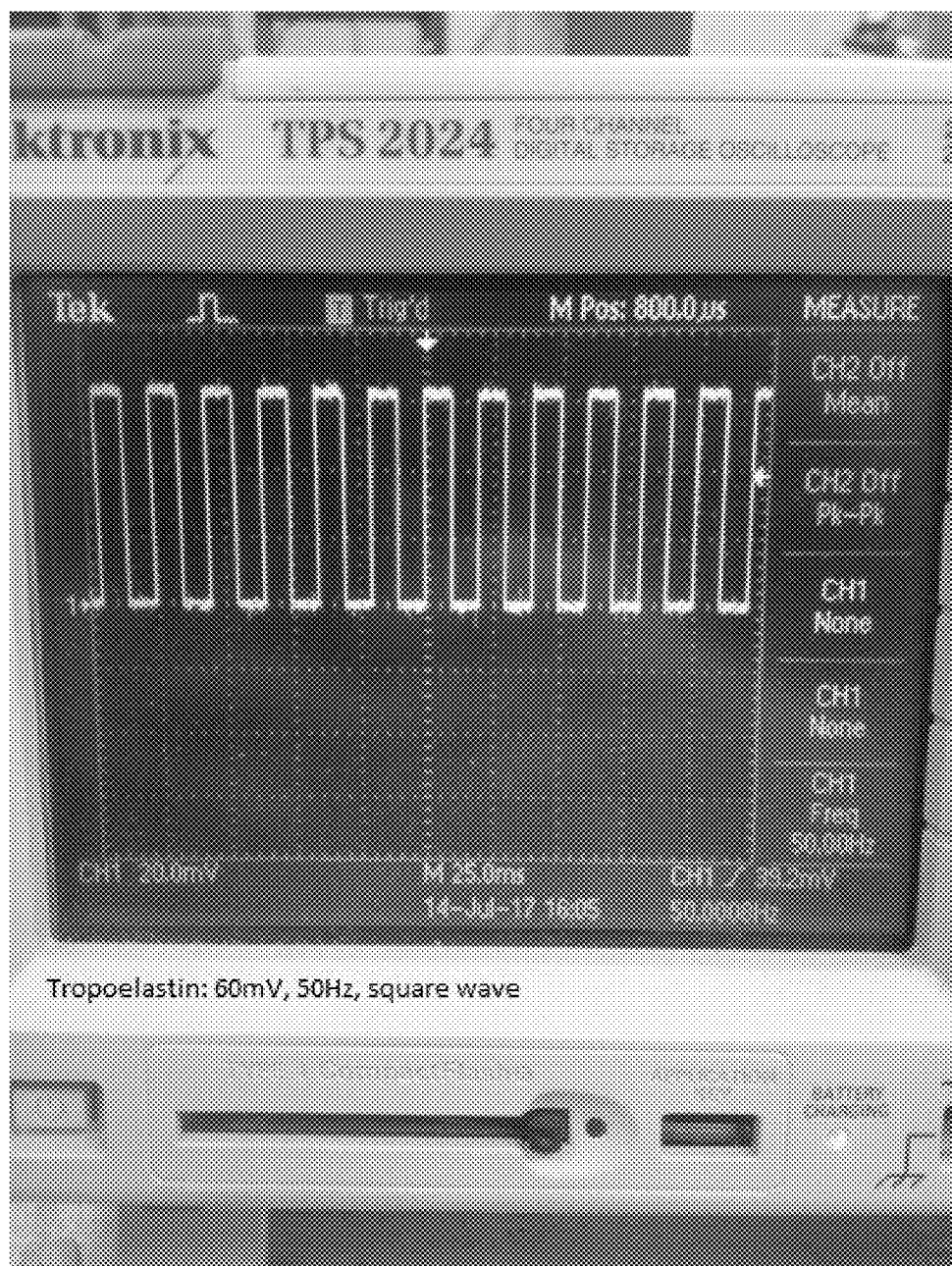
FIG. 10 depicts an image of the signal (voltage and frequency) associated with tropoelastin: 60 mV, 50 Hz, square wave.
Figure 11:
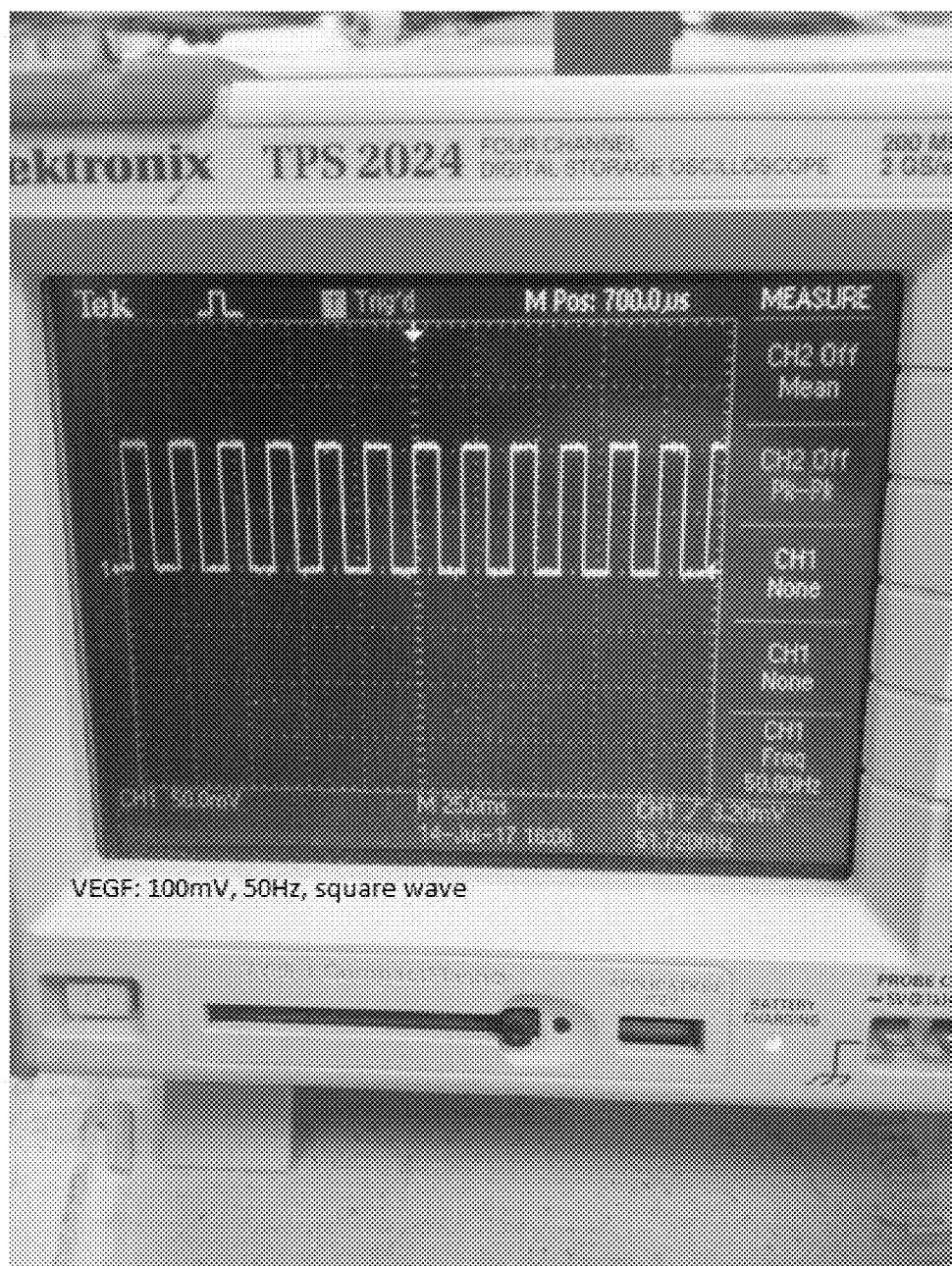
FIG. 11 depicts an image of the signal (voltage and frequency) associated with VEGF: 100 mV, 50 Hz, square wave.
Figure 12:
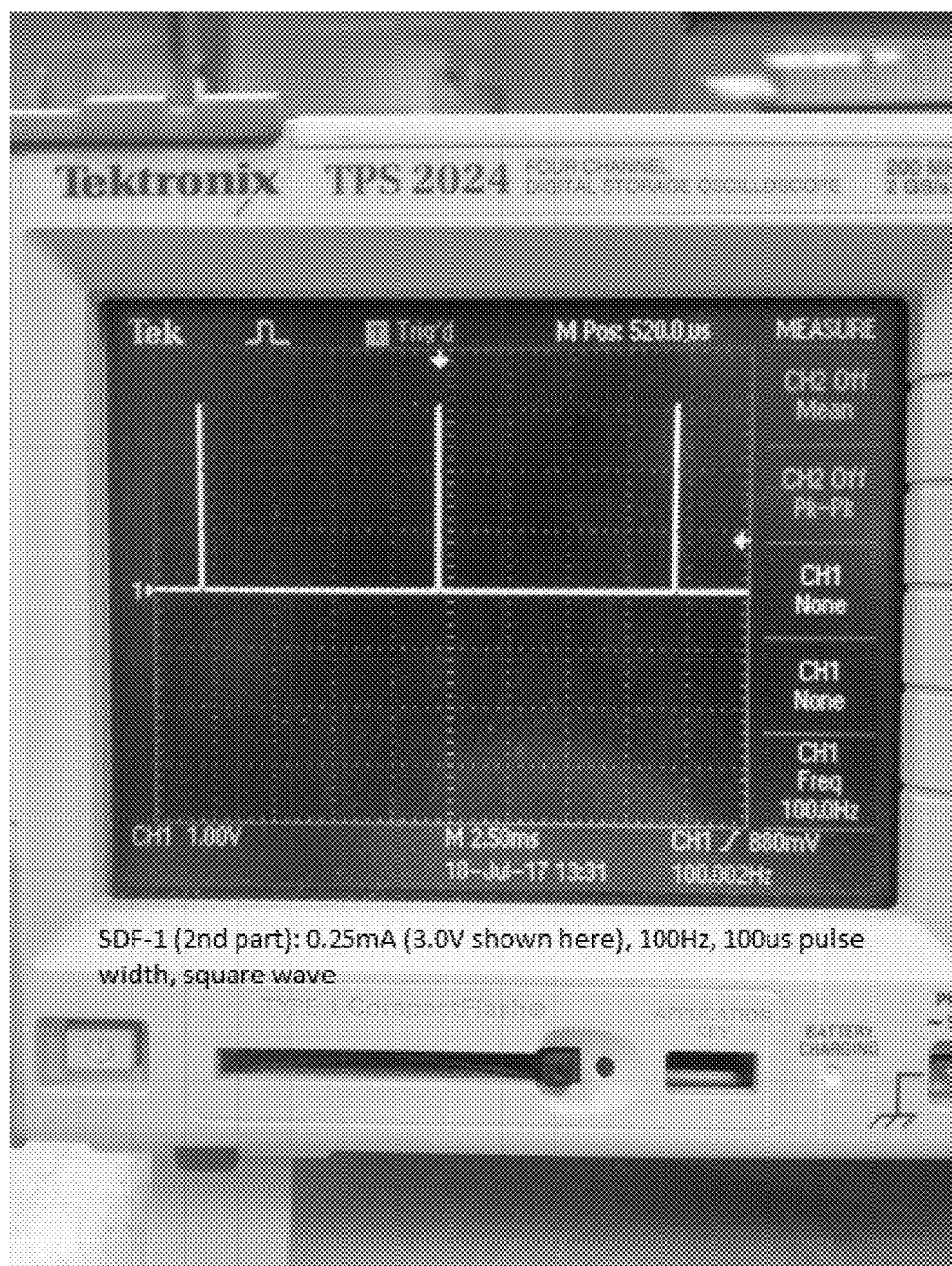
FIG. 12 depicts an image of the signal (voltage and frequency) associated with SDF-1 ($2^{nd}$ part): 0.25 mA (3.0 V shown here), 100 Hz, 100 µs pulse width, square wave.

Specifically, FIG. 3 depicts an image of the signal (voltage and frequency) associated with EGF at 10 V/cm (5 V here), 500 Hz, pulse width 180 µs, square wave. FIG. 4 depicts an image of the signal (voltage and frequency) associated with follistatin at 10 V/cm, 50 Hz, square wave. FIG. 5 depicts an image of the signal (voltage and frequency) associated with HGF at 3.5 V, 10 second burst every 30 seconds, square wave. FIG. 6 depicts an image of the signal (voltage and frequency) associated with IGF-1: 3.0 mV, 22 Hz, square wave. FIG. 7 and FIG. 8 relate to PDGF signals. FIG. 9 depicts an image of the signal (voltage and frequency) associated with SDF-1: 3.5 mV, 30 Hz, square wave. FIG. 10 depicts an image of the signal (voltage and frequency) associated with tropoelastin: 60 mV, 50 Hz, square wave. FIG. 11 depicts an image of the signal (voltage and frequency) associated with VEGF: 100 mV, 50 Hz, square wave. FIG. 12 depicts an image of the signal (voltage and frequency) associated with SDF-1 ($2^{nd}$ part): 0.25 mA (3.0 V shown here), 100 Hz, 100 µs pulse width, square wave.

In certain embodiments, a subject's organ(s) and/or tissue (s) are first scanned or analyzed with a device to determine what his or her needs may be before treatment begins. The scanning/analysis can be by, e.g., generating mechanical vibrations at position adjacent the location to be an analyzed as described in, e.g., U.S. 2003/0220556 A1 to Porat et al. (the contents of which are incorporated herein by this reference) and/or by measuring transmembrane voltage potential of a cell (see, e.g., Chernet & Levin, "Transmembrane voltage potential is an essential cellular parameter for the detection and control of tumor development in a Xenopus model," Dis. Models and Mech. 6, pp. 595-607 (2013); doi:10.1242/dmm.010835, the contents of which are also incorporated herein by this reference. See, also, Brooks et al. "Bioelectric impedance predicts total body water, blood pressure, and heart rate during hemodialysis in children and adolescents," J. Ren. Nutr., 18(3):304-311 (May 2008); doi: 10.1053/j.jrn.2007.11.008, the contents of which are incorporated herein by this reference, describing the use of bioelectric impedance to evaluate the variability of blood pressure, systolic blood pressure, etc.

As used herein, "scanning" means measuring bioelectrical electrical activity of organs, sometimes by placement of a bion coil reader and transmitter in the organ, and direct that information to a computer. The computer stores the bioelectrical read measurements of diseased organs and healthy organs and makes a comparative exam classifying the organ into one category or another, which is much like a doctor using information to make a diagnosis.

Presently, the best approach for whole body and individual organ scanning is to use a combination of: (a) 3D Body Scannint, (b) Quantum Magnetic Resonance Scanning, (c) Biofeedback scanning, (d) Bioelectric scanning, (e) Bion implant scanning, (f) Nervous system scanning, and (g) Light-activated cell reaction reading.

Scanners such as the Ina'Chi scanner, the Quantum Magnetic Resonance Analyzer (QMRA), the 3D Quantum Health Analyzer Scan whole body organ health 2, Body-Scan® scanner, and the "BIONic muscle spindle" are also useful.

See, also, P. Collins, "Bioelectric Signals Can Be Used to Detect Early Cancer," *Tufts News*, http://now.tufts.edu/news-releases/bioelectric-signals-used-detect-early-cancer (Feb. 1, 2013) reported that scientists had discovered a bioelectric signal that can identify cells likely to develop into tumors, and that they could lower the incidence of cancerous cells by manipulating the electrical charge across cell membranes. After the subject's needs in this regard are determined, then treatment (e.g., enhanced tissue growth or regeneration) may be initiated as needed and/or desired, preferably with the same device.

In an alternative embodiment, the analysis conducted by the device comprises (or further includes) detecting minute energy fields around the human body with, e.g., a "SQUID magnetometer" (SQUID is an acronym for "Superconducting Quantum Interference Device"), able to detect biomagnetic fields associated with physiological activities in the subject's body. A quantum resonant magnetic analyzer analyzes such fields. The magnetic frequency and energy of a subject's organ(s) and/or tissue(s) are collected by appropriately positioning the sensor with respect to the portion of the subject's organ(s) and/or tissue(s) to be analyzed, and after amplification of the signal by the instrument, the data are compared with standard quantum resonant spectrum of diseases, nutrition, and other indicators/markers to determine whether the sample waveforms are irregular using a Fourier approach.

The invention is further described with the aid of the following illustrative Examples.

EXAMPLES

Example—Controlling Expression of Follistatin

Low voltage pulsed electrical stimulation device for controlling expression of follistatin, a muscle formation promotion protein, from tissues.

Epicardial stimulation is especially useful for heart regeneration.

In one embodiment, the system stimulates the controlled production/release of follistatin, a known myostatin inhibitor, thus promoting the formation of new muscle and repair of damaged or weakened muscle including heart muscle post heart attack. Follistatin-like 1 (FSTL1) is a protein that encourages the growth of healthy cells, contractile muscle tissue and even blood vessels, helping supply the newly created muscle tissue with oxygen and nutrients. This therapy was originally designed to reduce or eliminate scarring of the heart following a heart attack and reversing heart failure, but may also be applicable to treating other organs suffering from muscle loss or degradation.

The electrical stimulation device promotes the reliable controlled release of follistatin with practical, safe, low voltages. The version of the system described in this Example includes the following components: Micro voltage signal generator (micro-stimulator from QIG Greatbatch); pacing and infusion lead; corkscrew tip; conductive polymer bandage wrap or patch; signal programmer; and external battery charging wand.

Relationship Between the Components

The micro voltage signal generator is attached to the pacing infusion lead with, e.g., a corkscrew tip or conductive polymer bandage or patch to the tissue or organ to be treated. An external signal programmer may be used to program the micro voltage signal generator with the proper signals for treatment including the follistatin producing signal. The device battery may be re-chargeable with an external battery charging wand.

In use, the signal generator sends a signal to the target tissue organ that causes the genes within the DNA of that tissue to start the follistatin synthesis process on demand. The signal generator sends a signal to the target tissue organ that causes the genes within the DNA of that tissue to start releasing follistatin on demand. The follistatin—(muscle growth) production signal is preferably 10 V at 50 HZ and 100 HZ 0.25 mA alternating back and forth. A 3 V signal is being developed.

The system not only controls the DNA to build ribosomes and proteins, but also controls the gates of the cell membranes opening and closing correctly to promote regeneration.

The essential elements are the micro voltage signal generator and the means for delivering the signal to the target tissue.

The signal generator may be external or internal. The transmission of the signal may be wireless, via liquid and/or via wires.

The tissue contact interface may be a patch or bandage or may be via electrodes or leads.

The described system produces follistatin under precise dosing control at safe and comfortable low voltages.

The signal generator programmed with the follistatin release signal is directed via a lead, bandage of patch to the target organ tissue in need of muscle repair or build up. As the signal is in stimulation mode the tissue releases follistatin and muscle is built or repaired as needed until full function resumes or the desired enhanced function is reached.

EXAMPLE

A human subject's blood pressure is monitored. The device of FIG. 2 (or FIG. 1) is utilized to deliver bioelectric signals to fibers in the subject's vagal nerve. These bioelectric signals include the signals for the subject's tissue to enhance the control and/or release of tropoelastin, SDF-1, VEGF, IGF-1, PDGF and HGF. The subject's blood pressure is controlled.

REFERENCES (The contents of the entirety of each of which is incorporated herein by this reference.)

AlGhatrif et al., "The Conundrum of Arterial Stiffness, Elevated blood pressure, and Aging," *Curr. Hypertens. Rep.* 2015 February; 17(2): 12; doi: 10.1007/s11906-014-0523-z.

Greenwald, S.E., "Pulse pressure and arterial elasticity," *QJM: An International Journal of Medicine*, 95(2): 107-112 (1 Feb. 2002); doi://doi.org/10.1093/qjmed/95.2.107.

Sethi et al., "Aortic stiffness: pathophysiology, clinical implications, and approach to treatment," *Integr. Blood Press. Control.* 2014; 7: 29-34; doi: 10.2147/IBPC.S59535.

Welch W. J., "RGS2 Proteins Regulate Blood Pressure," *JASN*, November 2010, 21(11):1809-1810; doi: //doi.org/10.1681/ASN.2010090977.

U.S. Pat. No. 6,957,106 to Schuler et al. (Oct. 18, 2005) describes inter alia a method and device for modulating blood pressure. The method comprises selecting waveforms from a storage area that are representative of body organ function. The selected waveforms are then transmitted to a treatment member, which is in direct contact with the body, and which then broadcasts the waveforms to blood pressure regulatory points within the body to modulate blood pressure. A control module is provided for transmission to the treatment member. The control module contains the waveforms which are selected and transmitted to the treatment member, and computer storage can be provided for greater storage capacity and manipulation of the waveforms.

U.S. Patent Application Publication number 20040236238 to Schuler et al. (Feb. 18, 2004) describes inter alia a method and device for modulating blood pressure. The method comprises selecting waveforms from a storage area that are representative of body organ function. The selected waveforms are then transmitted to a treatment member, which is in direct contact with the body, and which then broadcasts the waveforms to blood pressure regulatory points within the body to modulate blood pressure. A control module is provided for transmission to the treatment member. The control module contains the waveforms which are selected and transmitted to the treatment member, and computer storage can be provided for greater storage capacity and manipulation of the waveforms.

Salcedo et al., "Low current electrical stimulation upregulates cytokine expression in the anal sphincter," *Int. J. Colorectal Dis.*, 2012 February; 27(2):221-5. doi: 10.1007/s00384-011-1324-3. Epub (October 2011).

Hopkins Medicine, "Overview of Pacemakers and Implantable Cardioverter Defibrillators (ICDs)," hopkinsmedicine.org/healthlibrary/conditions/cardiovascular_diseases/overview_of_pacemakers_and_implantable_cardioverter_defibrillators_icds_85,P00234/.

Medtronic, "Cardiac Resynchronization Therapy (CRT) Devices For Heart Failure," medtronic.com/us-en/patients/treatments-therapies/crt-devices.html.

H.N. Sabbah, "Electrical vagus nerve stimulation for the treatment of chronic heart failure," *Cleve. Clin. J. Med.*, 78 Suppl. 1:S24-9. doi: 10.3949/ccjm.78.s1.04 (Aug 2011).

Bio-Leonhardt, "Micro Stimulator" bioleonhardt.com/micro-stimulator/.

H. U. Klein, "Vagus Nerve Stimulation: A new approach to reduce heart failure," *Cardiology Journal* (2010).

Cerrada et al., "Hypoxia-Inducible Factor 1 Alpha Contributes to Cardiac Healing in Mesenchymal Stem Cells-Mediated Cardiac Repair," *Stem Cells and Development*, 22(3): 501-511 (2013).

Fatemi et al., "Imaging elastic properties of biological tissues by low-frequency harmonic vibration," *Proceedings of the IEEE*, 91(10):1503-1519 (October 2003) DOI: 10.1109JPROC.2003.817865.

Kido et al., "Hypoxia-Inducible Factor 1-Alpha Reduces Infarction and Attenuates Progression of Cardiac Dysfunction After Myocardial Infarction in the Mouse," *JACC*, Volume 46, Issue 11, 6 Dec. 2005, Pages 2116-2124. https://doi.org/10.1016/j.jacc.2005.08.045.

Mosteiro et al., "Tissue damage and senescence provide critical signals for cellular reprogramming in vivo," Science, 2016; 354 (6315): aaf4445 DOI: 10.1126/science.aaf4445

Tajima et al., "HIF1alpha is necessary to support gluconeogenesis during liver regeneration," *Biochem. Biophys. Res. Commun.* 2009 Oct. 2; 387(4):789-94. doi: 10.1016/j.bbrc.2009.07.115. Epub 2009 Jul. 28.

What is claimed is:

1. A method of using a bioelectric stimulator to control blood pressure in a subject, wherein the bioelectric stimulator comprises: a power source and means for delivering bioelectric signals to the subject's tissue, wherein the bioelectric stimulator utilizes the electrical signal to upregulate protein expression in the subject's tissue on demand so as to control blood pressure in the subject, the method comprising:

physically associating the bioelectric stimulator with tissue of the subject; and delivering selected bioelectric signals to the subject's tissue from the bioelectric stimulator so as to control the expression of proteins, wherein the proteins comprise stromal cell-derived factor 1 ("SDF1"), vascular endothelial growth factor ("VEGF"), insulin-like growth factor 1 ("IGF1"), platelet-derived growth factor ("PDGF"), tropoelastin, and hepatocyte growth factor ("HGF").

2. The method according to claim 1, further comprising:
wherein the proteins further comprise a protein selected from the group consisting of IGF1, epidermal growth factor ("EGF"), endothelial NOS ("eNOS"), follistatin, and a combination of any thereof.

3. The method according to claim 1, wherein the subject's tissue comprises fibers inside the vagus nerve.

4. The method according to claim 3, wherein the subject's tissue does not comprise non-baroreceptive fibers.

5. The method according to claim 1, wherein the subject's tissue does not comprise non-baroreceptive fibers.

6. A method of controlling blood pressure in a subject, the method comprising:

delivering selected bioelectric signals to the subject's tissue so as to enhance the expression of proteins, wherein the proteins comprise stromal cell-derived factor 1 ("SDF1"), vascular endothelial growth factor ("VEGF"), insulin-like growth factor 1 ("IGF1"), platelet-derived growth factor ("PDGF"), tropoelastin, and hepatocyte growth factor ("HGF").

7. The method according to claim 6, further comprising:
delivering selected bioelectric signals to the subject's tissue so as to enhance the release and/or expression of a protein selected from the group consisting of IGF1, epidermal growth factor ("EGF"), endothelial NOS ("eNOS"), follistatin, and a combination of any thereof.

8. The method according to claim 6, wherein the subject's tissue comprises fibers inside the vagus nerve.

9. The method according to claim 8, wherein the subject's tissue does not comprise non-baroreceptive fibers.

10. The method according to claim 6, wherein the subject's tissue does not comprise non-baroreceptive fibers.

11. A method of controlling blood pressure in a subject, the method comprising:

delivering selected bioelectric signals to the subject's tissue, wherein the bioelectric signals comprise the following:

(a) (within 15%) 30 Hz, square wave and/or 100 Hz, 100 μs pulse width, square wave;
(b) 50 Hz, square wave;
(c) (within 15%) 22 Hz, square wave; and
(d) 10 Hz, pulse width 200 μs, square wave and/or 100 Hz, pulse width 100 μs, square wave.

12. The method according to claim 11, wherein the bioelectric signals further comprise:

bioelectric signal(s) selected from the group consisting of (within 15%) 10 V/cm, 500 Hz, pulse width 180 μs, square wave;

0.25 mA, 100 Hz, 100 μs pulse width, square wave;

(within 15%) alternating high-frequency and medium-frequency signals, symmetric, biphasic, trapezoid pulses, with 400-μs pulse duration and 1.5/1-s ramp-up/ramp-down duration, respectively (wherein the electrical signal is as measured three (3) mm deep into the tissue); and a combination of any thereof.

13. The method according to claim 11, wherein the subject's tissue comprises fiber inside the vagus nerve.

14. The method according to claim 13, wherein the subject's tissue does not comprise non-baroreceptor fibers.

15. The method according to claim 11, wherein the subject's tissue does not comprise non-baroreceptor fibers.

16. The method according to claim 11, wherein the bioelectric signals further comprise a bioelectric signal of, within 15%, 500 Hz, pulse width 180 μs, square wave.

17. The method according to claim 11, wherein the bioelectric signals further comprise a bioelectric signal of 100 Hz, 100 μs pulse width, square wave.

18. The method according to claim 11, wherein the bioelectric signals further comprise a bioelectric signal of, within 15%, alternating high-frequency (HF) and medium-frequency signals (MF), symmetric, biphasic, trapezoid pulses, with 400-μs pulse duration and 1.5/1-s ramp-up/ramp-down duration, respectively (wherein the electrical signal is as measured three (3) mm deep into the tissue).

* * * * *